United States Patent [19]
Meserol

[11] Patent Number: 5,720,921
[45] Date of Patent: Feb. 24, 1998

[54] FLOW ELECTROPORATION CHAMBER AND METHOD

[75] Inventor: Peter M. Meserol, Montville, N.J.

[73] Assignee: Entremed, Inc., Rockville, Md.

[21] Appl. No.: 402,145

[22] Filed: Mar. 10, 1995

[51] Int. Cl.[6] ................................................. C12N 15/87
[52] U.S. Cl. ..................... 422/44; 435/173.6; 435/285.2; 604/4; 935/85
[58] Field of Search .......................... 422/44, 109, 111; 435/2, 173.1, 173.6, 287, 289, 285.2; 204/299 R, 183.1; 935/85; 604/4

[56] References Cited

U.S. PATENT DOCUMENTS

| | | | |
|---|---|---|---|
| 2,955,076 | 10/1960 | Gossling | 935/85 X |
| 4,075,076 | 2/1978 | Xylander | 204/206 |
| 4,081,340 | 3/1978 | Zimmerman et al. | 204/299 X |
| 4,192,869 | 3/1980 | Nicolau | 424/199 |
| 4,321,259 | 3/1982 | Nicolau | 424/101 |
| 4,473,563 | 9/1984 | Nicolau | 424/224 |
| 4,478,824 | 10/1984 | Franco et al. | 424/101 |
| 4,622,302 | 11/1986 | Sowers | 435/172.2 |
| 4,652,449 | 3/1987 | Ropars | 424/101 |
| 4,695,547 | 9/1987 | Hilliard et al. | 435/173 |
| 4,699,881 | 10/1987 | Matschke | 435/173 |
| 4,752,586 | 6/1988 | Ropars et al. | 435/287 |

(List continued on next page.)

FOREIGN PATENT DOCUMENTS

| | | | |
|---|---|---|---|
| 0 137 504 | 4/1985 | European Pat. Off. | 435/173 |
| 0 343 783 | 11/1989 | European Pat. Off. | 435/173 |
| 0 362 758 | 4/1990 | European Pat. Off. | 435/173 |
| 2405119 | 9/1975 | Germany | 435/173 |

(List continued on next page.)

OTHER PUBLICATIONS

Gersonde, et al., *Enhancement of the $O_2$ Release Capacity and of the Bohr-Effect of Human Red Blood Cells after Incorporation of Inositol Hexaphosphate by Fusion with Effector-Containing Lipid Vesicles*, Hemoglobin and Oxygen Binding II Origins of Cooperative Binding By Hemoglobins, pp. 277–282 (1982).

Gersonde, et al., *Improvement of the Red Blood Cell $O_2$ Release Capacity by Lipid Vesicle-mediated Incorporation of Inositol Hexaphosphate*, BLUT, vol. 39 pp. 1–7, (1979).

Gersonde, et al., *Modification of the Oxygen Affinity of Intracellular Haemoglobin by Incorporation of Polyphosphates into Intact Red Blood Cells and Enhanced $O_2$ Release in the Capillary System*, Biblithca. Haematol., vol. 46, pp. 81–92, (1980).

Gersonde, et al., *The Influence of Infusion Rate on the Acute Intravenous Toxicity of Phytic Acid, A Calcium–Binding Agent*, Toxicology, vol. 22, pp. 279–286, (1982).

Lehninger, Albert L., *Principles of Biochemistry*, pp. 181–194, 705–711, 779 (1982).

Mouneimne, et al., *Stable Rightward Shifts of the Oxyhemoglobin Dissocation Curve Induced by Encapsulation of Inositol Hexaphosphate in Red Blood Cells Using Electroporation*, FEBS Letters, vol. 275, pp. 117–120 (1990).

(List continued on next page.)

*Primary Examiner*—Robert J. Warden
*Assistant Examiner*—E. Leigh Dawson
*Attorney, Agent, or Firm*—Jones & Askew, LLP

[57] ABSTRACT

The present invention relates to a method and apparatus for the encapsulation of biologically-active substances in red blood cells, characterized by an optionally automated, continuous-flow, self-contained electroporation system which allows withdrawal of blood from a patient, separation of red blood cells, encapsulation of a biologically-active substances in the cells, and optional recombination of blood plasma and the modified red blood cells thereby producing blood with modified biological characteristics. The present invention is particularly suited for use to encapsulate allosteric effectors of hemoglobin, thereby reducing the affinity of erythrocytes for oxygen and improving the release of oxygen from erythrocytes in tissues.

6 Claims, 13 Drawing Sheets

U.S. PATENT DOCUMENTS

| | | | |
|---|---|---|---|
| 4,764,473 | 8/1988 | Matschke et al. | 435/287 |
| 4,784,737 | 11/1988 | Ray et al. | 204/299 X |
| 4,800,163 | 1/1989 | Hibi et al. | 435/287 |
| 4,804,450 | 2/1989 | Mochizuki et al. | 204/299 R |
| 4,822,470 | 4/1989 | Chang | 204/299 R |
| 4,849,089 | 7/1989 | Marshall, III | 204/299 R |
| 4,849,355 | 7/1989 | Wong | 435/172.3 |
| 4,874,690 | 10/1989 | Goodrich et al. | 435/2 |
| 4,882,281 | 11/1989 | Hilliard et al. | 435/173 X |
| 4,906,576 | 3/1990 | Marshall, III | 435/287 |
| 4,910,140 | 3/1990 | Dower | 435/173 |
| 4,923,814 | 5/1990 | Marshall, III | 435/173 |
| 4,931,276 | 6/1990 | Franco et al. | 435/2 X |
| 4,945,050 | 7/1990 | Sanford | 435/172.1 |
| 4,946,793 | 8/1990 | Marshall, III | 435/291 |
| 4,956,288 | 9/1990 | Barsoum | 435/172.3 |
| 4,970,154 | 11/1990 | Chang | 435/172.2 |
| 5,036,006 | 7/1991 | Sanford | 435/170.1 |
| 5,043,261 | 8/1991 | Goodrich et al. | 435/2 |
| 5,098,843 | 3/1992 | Calvin | 435/287 |
| 5,100,627 | 3/1992 | Buican et al. | 422/108 |
| 5,100,792 | 3/1992 | Sanford | 435/172.1 |
| 5,114,681 | 5/1992 | Bertoncini et al. | 422/111 |
| 5,124,259 | 6/1992 | Tada | 435/172.1 |
| 5,128,257 | 7/1992 | Baer | 435/173 |
| 5,135,667 | 8/1992 | Schoendorfer | 210/782 |
| 5,137,817 | 8/1992 | Busta et al. | 435/173 |
| 5,139,684 | 8/1992 | Kaali et al. | 422/44 X |
| 5,232,856 | 8/1993 | Firth . | |
| 5,424,209 | 6/1995 | Kearney | 435/284 |

FOREIGN PATENT DOCUMENTS

| | | | |
|---|---|---|---|
| 62-2171687 | 7/1987 | Japan | 435/173 |
| 62-2228277 | 10/1987 | Japan | 435/173 |
| 62-2265975 | 11/1987 | Japan | 435/173 |
| 63-3049068 | 3/1988 | Japan | 435/173 |
| 63-3141587 | 6/1988 | Japan | 435/173 |
| 64-1141582 | 6/1989 | Japan | 435/173 |
| 2131584 | 5/1990 | Japan | 435/173 |
| 2131585 | 5/1990 | Japan | 435/173 |
| 2186993 | 7/1990 | Japan | 435/173 |
| 3195485 | 8/1991 | Japan | 435/173 |
| 4027393 | 1/1992 | Japan | 435/173 |
| 8804322 | 6/1988 | WIPO | 435/173 |
| 8902464 | 3/1989 | WIPO | 435/173 |
| 9118103 | 11/1991 | WIPO . | |

OTHER PUBLICATIONS

Nicolau, et al., *Incorporation of Allosteric Effectors of Hemoglobin in Red Blood Cells*. Biochemical and Physiological Effects. Oxygen Transport in Red Blood Cells. Proceedings of the 12th Aharon Katzir Katchalsky Conference, pp. 141–147 (1984); Biblthca Heamat., No. 51, pp. 92–107 (Karger, Basel 1985).

Nicolau, et al., *Short and Long Term Physiological Effects of Improved Oxygen Transport by Red Blood Cells Containing Inositol Hexaphosphate*, Phytic Acid: Chemistry and Applications, pp. 265–290 (1986).

Ropars, et al., *Improved Oxygen Delivery to Tissues and Iron Chelator Transport through the Use of Lysed and Resealed Red Blood Cells: A New Perspective on Cooley's Anemia Therapy*, Annals New York Acad. of Sci., vol. 445, pp. 304–315, 477–491 (1985).

Teisseire, et al., *Long–Term Physiological Effects of Enhanced $O_2$ Release by Inositol Hexaphosphate–loaded Erythrocytes*, Proc. Natl. Acad. Sci. USA, vol. 84, pp. 6894–6898 (1987).

Teisseire, et al., *Physiological Effects on High–$P_{50}$ Erythrocyte Transfusion on Piglets*, J. Appl. Physiol., vol. 58, pp. 1810–1817 (1985).

Weiner, Murray, *Right Shifting of Hb–$O_2$ Dissociation in Viable Red Blood Cells by Liposomal Technique*, Biology of the Cell, vol. 47, pp. 65–70 (1983).

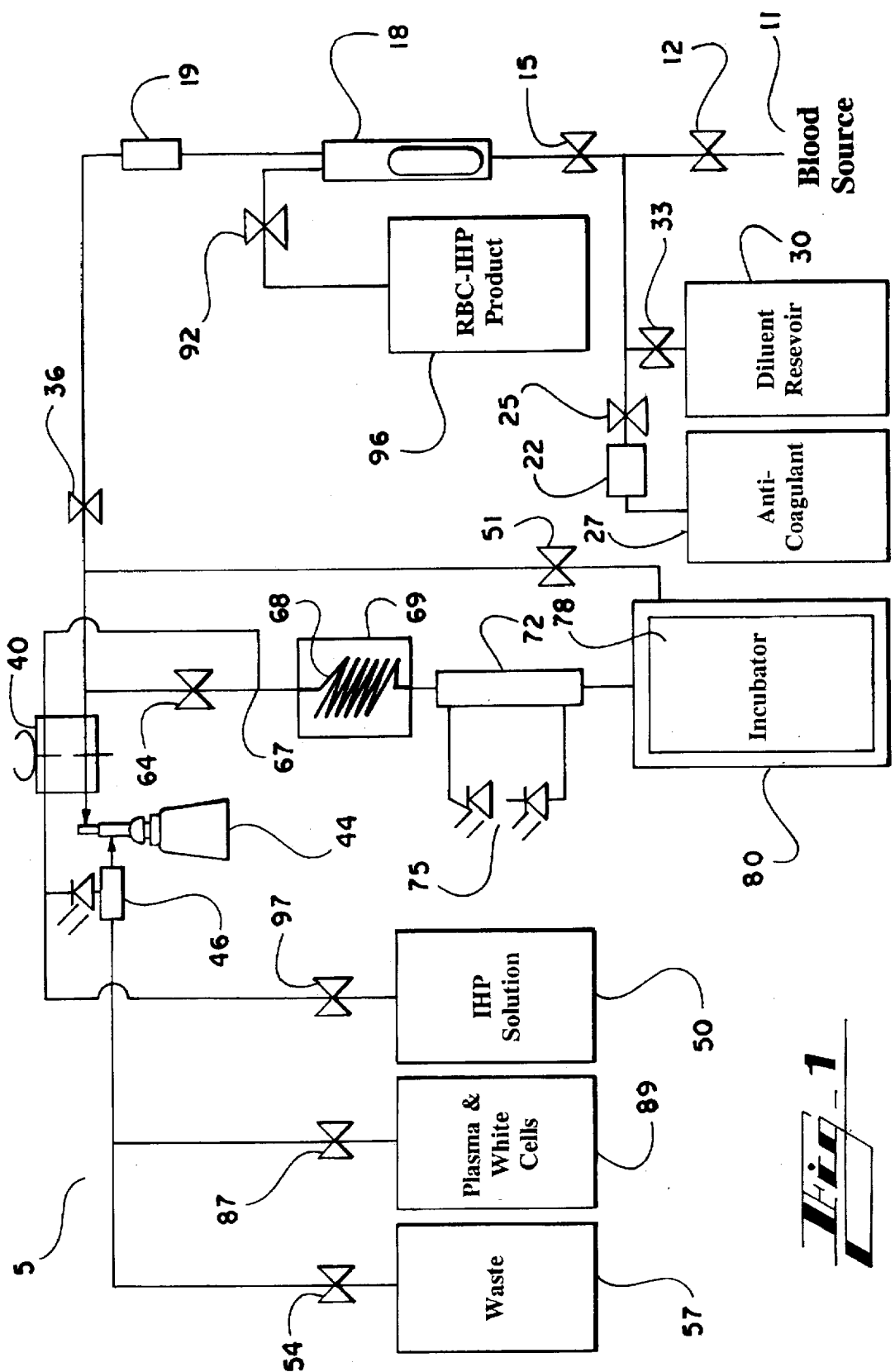

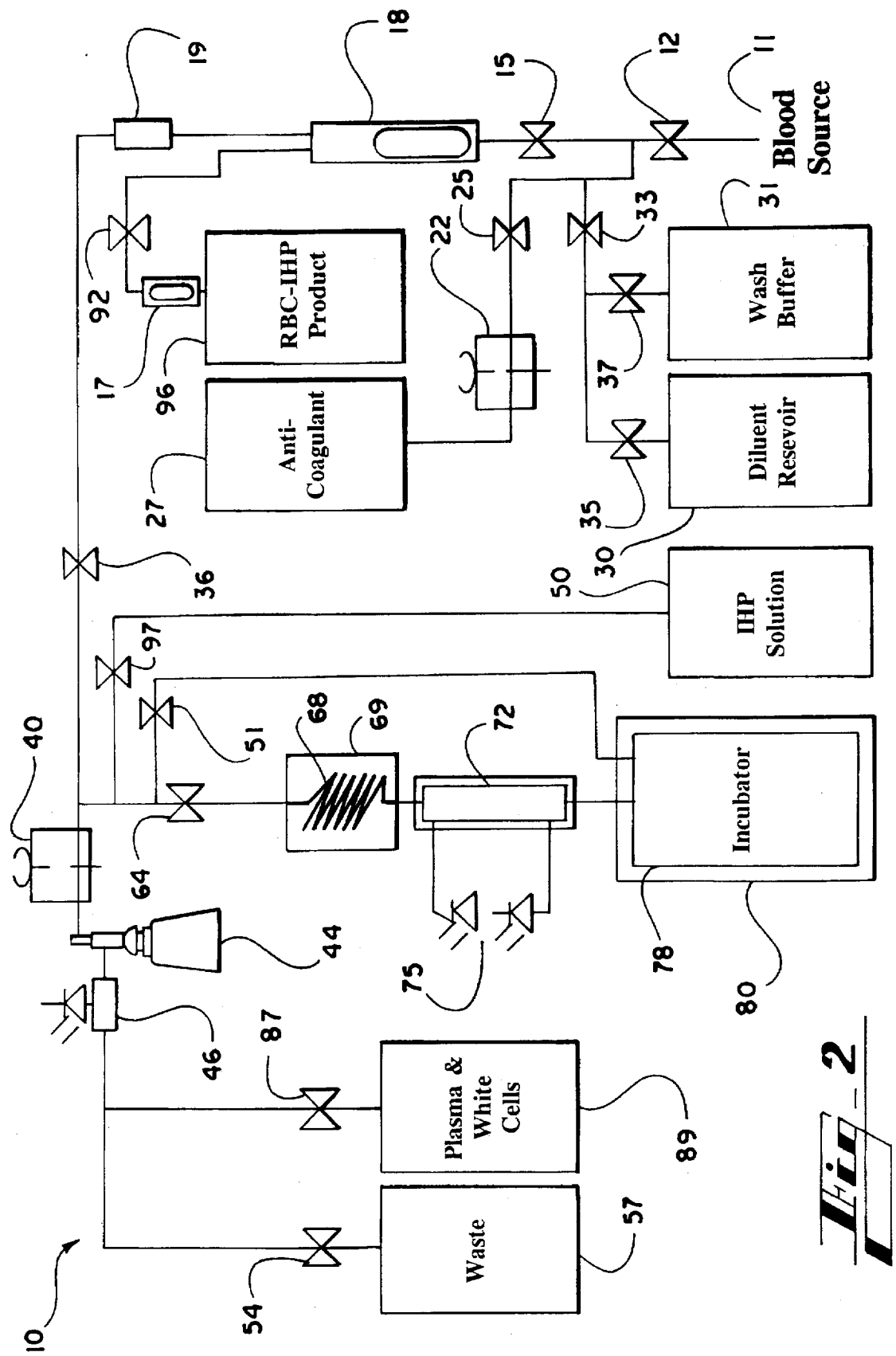

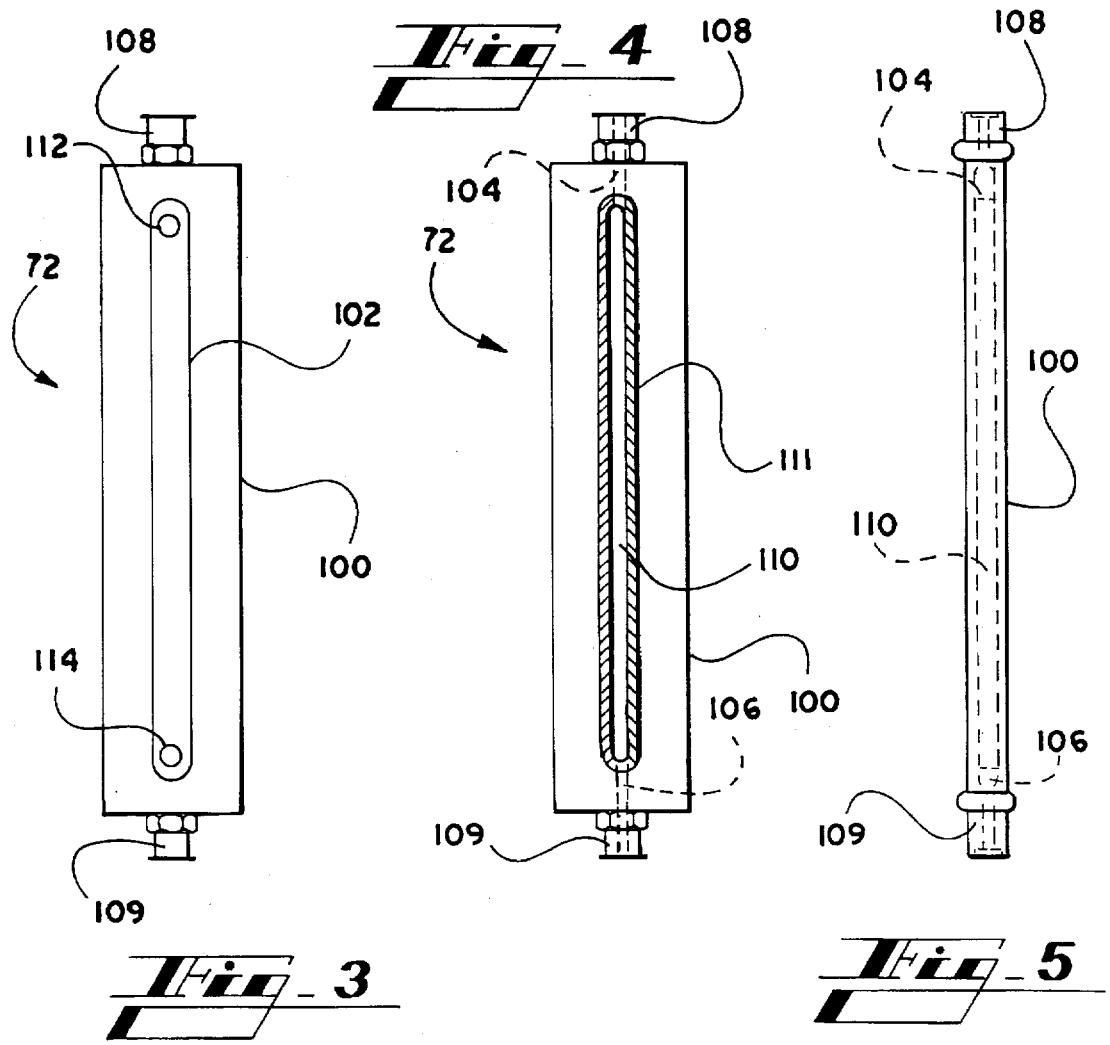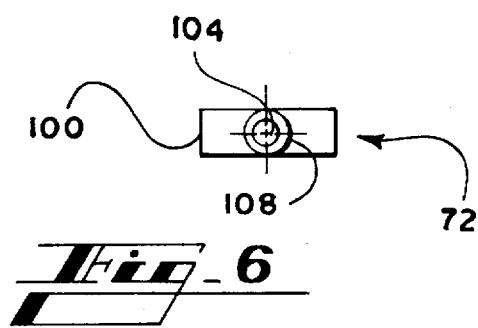

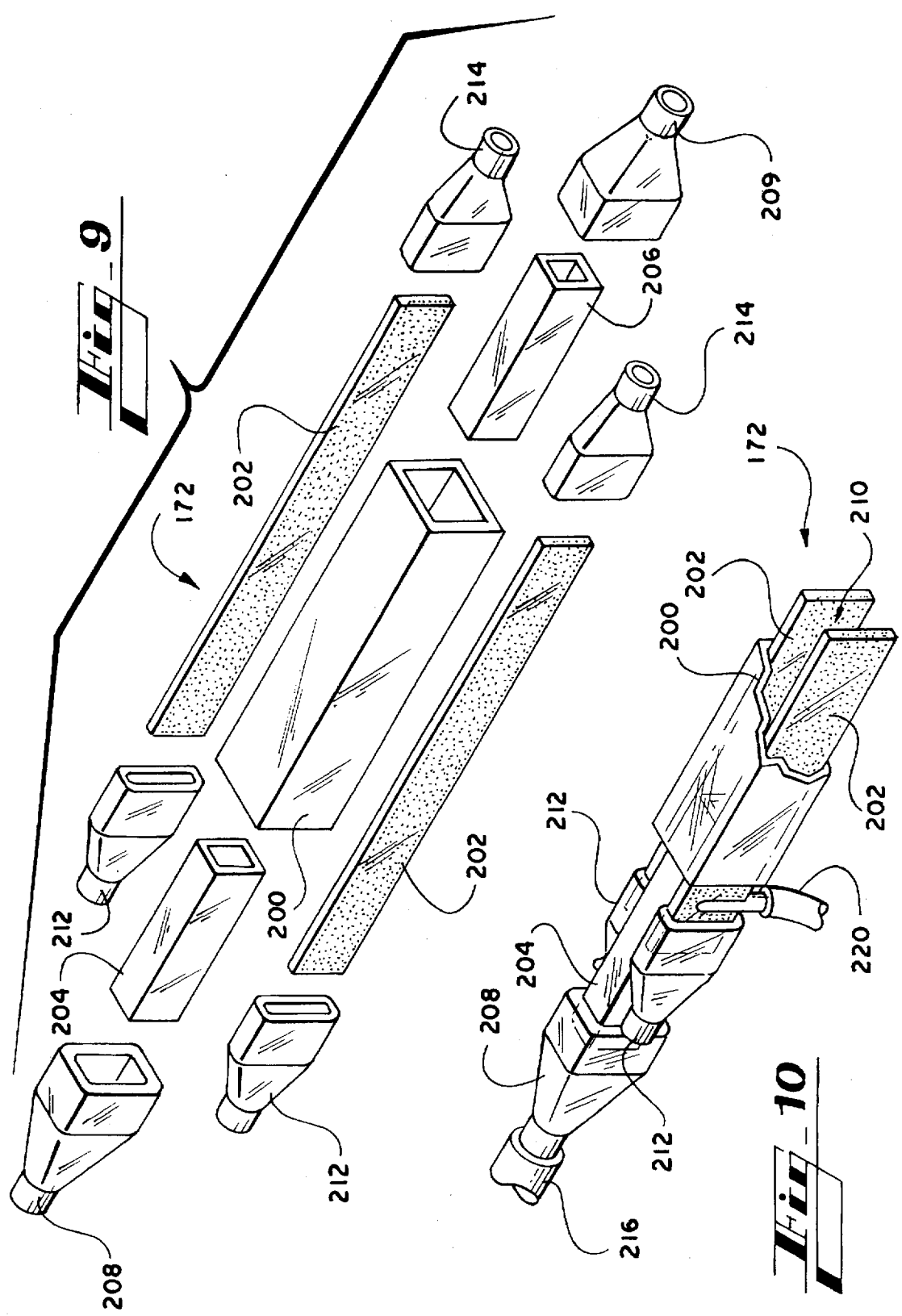

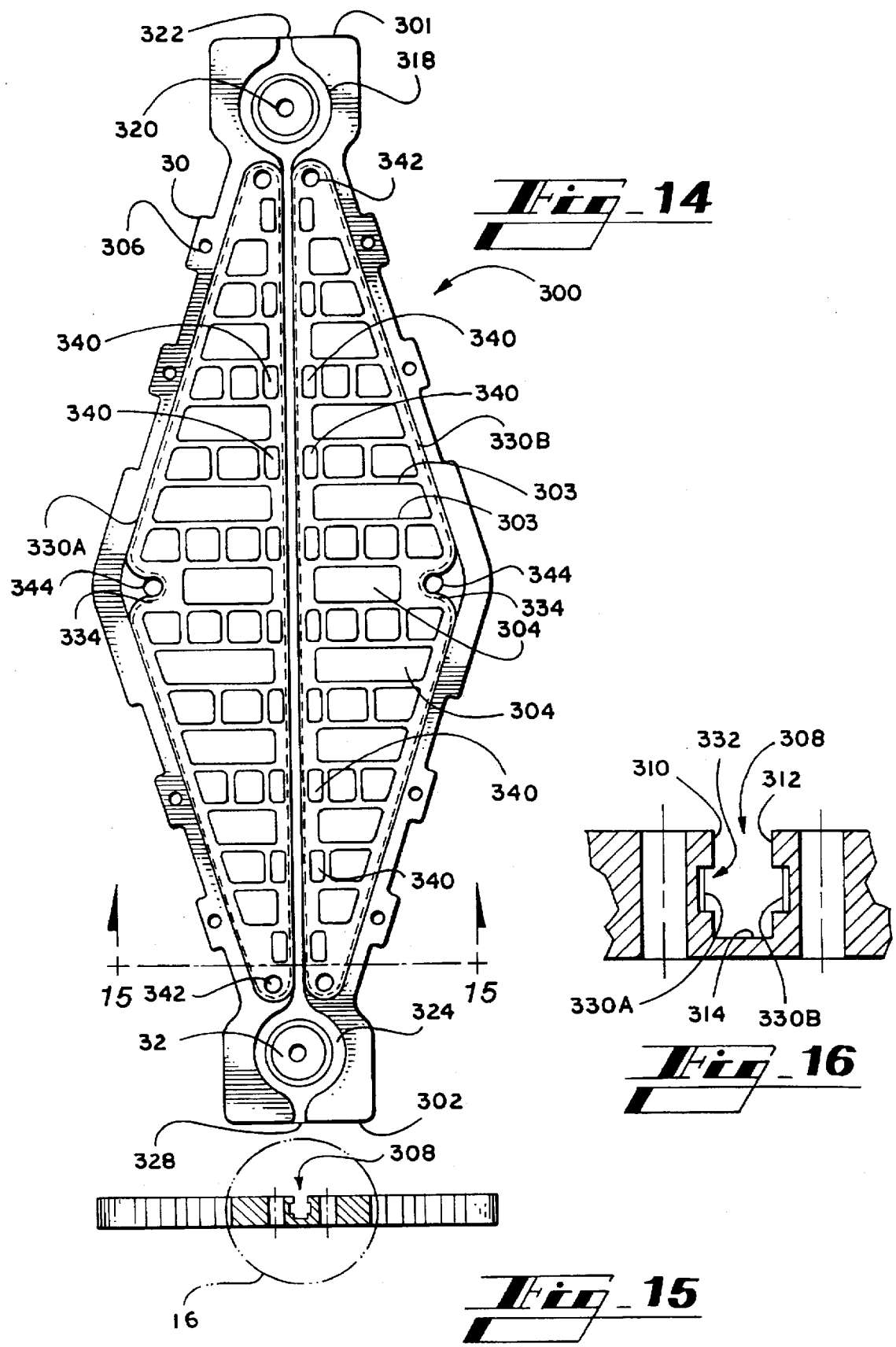

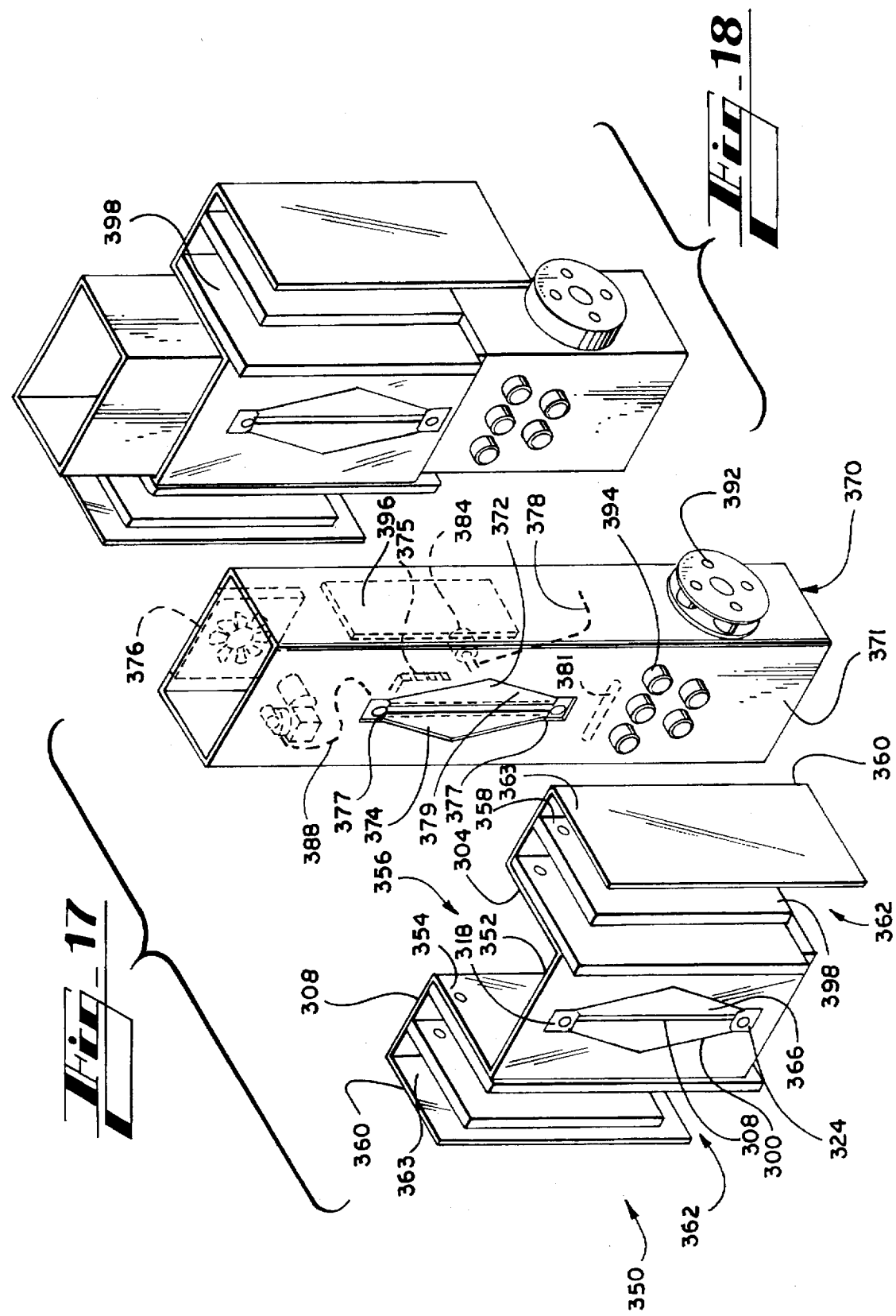

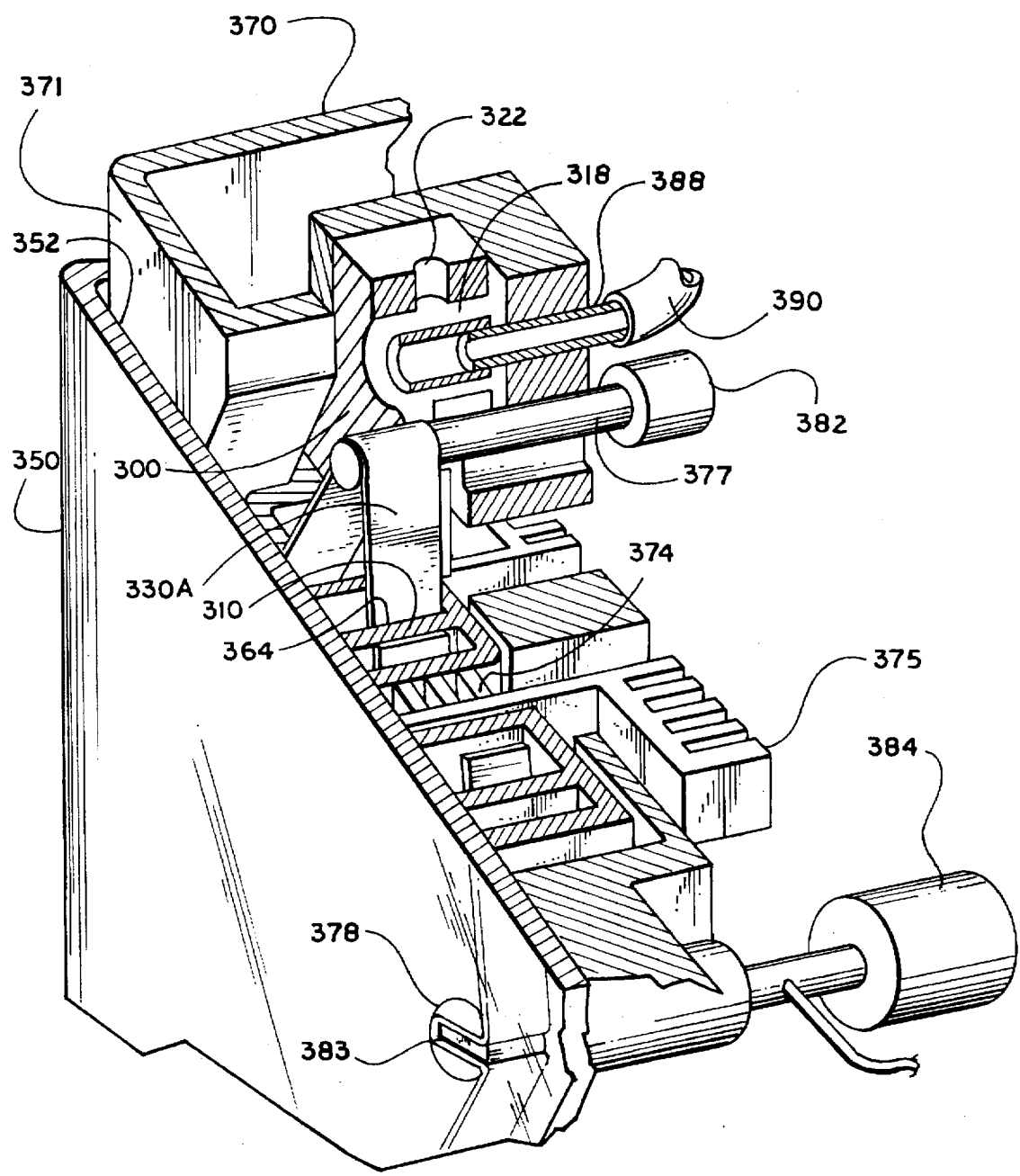
Fig_20

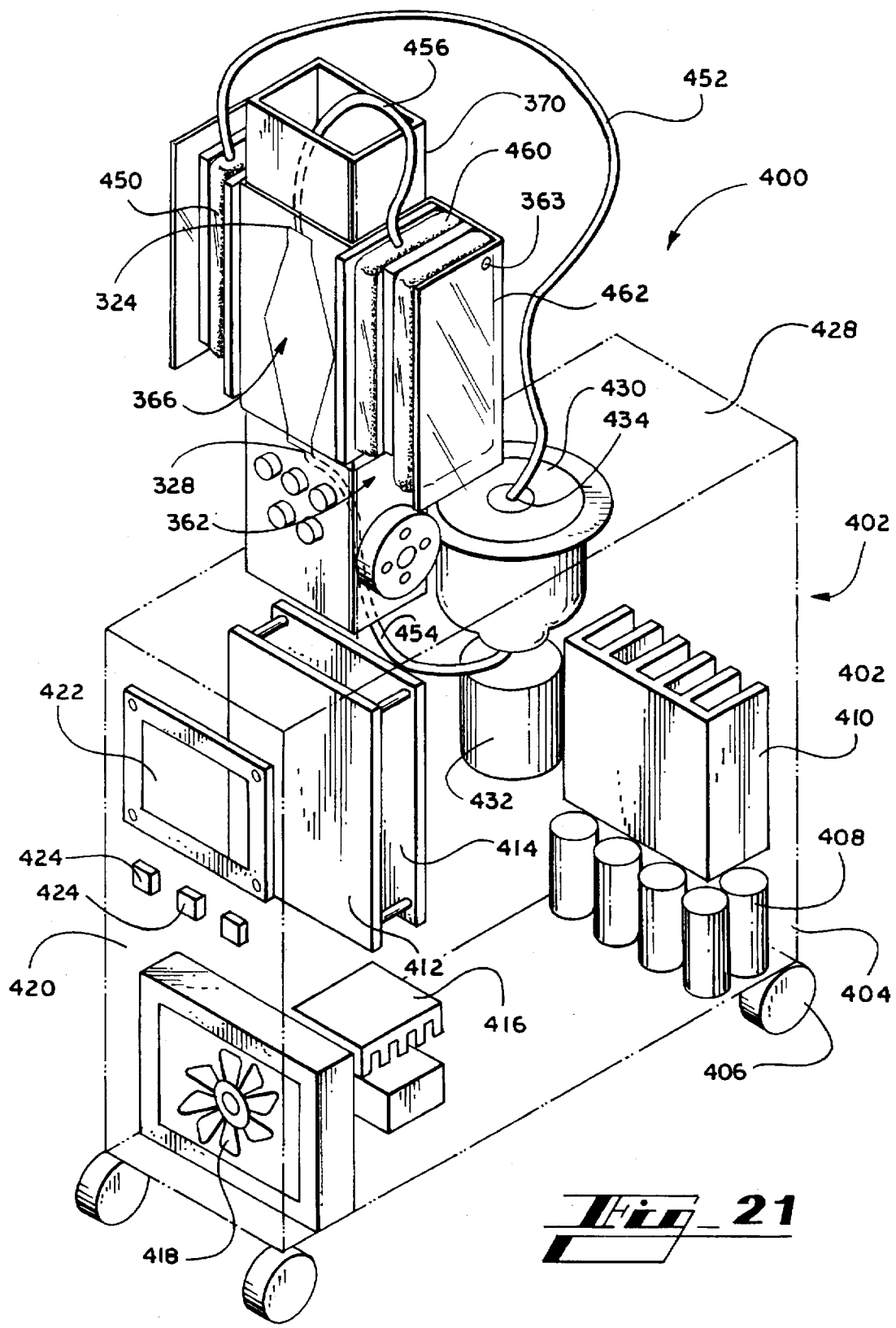
Fig_21

FLOW ELECTROPORATION CHAMBER AND METHOD

TECHNICAL FIELD

The present invention relates to methods and apparatus for the encapsulation of biologically-active substances in various cell populations. More particularly, the present invention relates to a method and apparatus for the encapsulation of allosteric effectors of hemoglobin in erythrocytes by electroporation to achieve therapeutically desirable changes in the physical characteristics of the intracellular hemoglobin.

BACKGROUND OF THE INVENTION

In the vascular system of an adult human being, blood has a volume of about 5 to 6 liters. Approximately one half of this volume is occupied by cells, including red blood cells (erythrocytes), white blood cells (leukocytes), and blood platelets. Red blood cells comprise the majority of the cellular components of blood. Plasma, the liquid portion of blood, is approximately 90 percent water and 10 percent various solutes. These solutes include plasma proteins, organic metabolites and waste products, and inorganic compounds.

The major function of red blood cells is to transport oxygen from the lungs to the tissues of the body, and transport carbon dioxide from the tissues to the lungs for removal. Very little oxygen is transported by the blood plasma because oxygen is only sparingly soluble in aqueous solutions. Most of the oxygen carried by the blood is transported by the hemoglobin of the erythrocytes. Erythrocytes in mammals do not contain nuclei, mitochondria or any other intracellular organelles, and they do not use oxygen in their own metabolism. Red blood cells contain about 35 percent by weight hemoglobin, which is responsible for binding and transporting oxygen.

Hemoglobin is a protein having a molecular weight of approximately 64,500 daltons. It contains four polypeptide chains and four heme prosthetic groups in which iron atoms are bound in the ferrous state. Normal globin, the protein portion of the hemoglobin molecule, consists of two α chains and two β chains. Each of the four chains has a characteristic tertiary structure in which the chain is folded. The four polypeptide chains fit together in an approximately tetrahedral arrangement, to constitute the characteristic quaternary structure of hemoglobin. There is one heme group bound to each polypeptide chain which can reversibly bind one molecule of molecular oxygen. When hemoglobin combines with oxygen, oxyhemoglobin is formed. When oxygen is released, the oxyhemoglobin is reduced to deoxyhemoglobin.

Delivery of oxygen to tissues depends upon a number of factors including, but not limited to, the volume of blood flow, the number of red blood cells, the concentration of hemoglobin in the red blood cells, the oxygen affinity of the hemoglobin and, in certain species, on the molar ratio of intraerythrocytic hemoglobins with high and low oxygen affinity. The oxygen affinity of hemoglobin depends on four factors as well, namely: (1) the partial pressure of oxygen; (2) the pH; (3) the concentration of the allosteric effective 2,3-diphosphoglycerate (DPG) in the hemoglobin; and (4) the concentration of carbon dioxide. In the lungs, at an oxygen partial pressure of 100 mm Hg, approximately 98% of circulating hemoglobin is saturated with oxygen. This represents the total oxygen transport capacity of the blood. When fully oxygenated, 100 ml of whole mammalian blood can carry about 21 ml of gaseous oxygen.

The effect of the partial pressure of oxygen and the pH on the ability of hemoglobin to bind oxygen is best illustrated by examination of the oxygen saturation curve of hemoglobin. An oxygen saturation curve plots the percentage of total oxygen-binding sites of a hemoglobin molecule that are occupied by oxygen molecules when solutions of the hemoglobin molecule are in equilibrium with different partial pressures of oxygen in the gas phase.

The oxygen saturation curve for hemoglobin is sigmoid. Thus, binding the first molecule of oxygen increases the affinity of the remaining hemoglobin for binding additional oxygen molecules. As the partial pressure of oxygen is increased, a plateau is approached at which each of the hemoglobin molecules is saturated and contains the upper limit of four molecules of oxygen.

The reversible binding of oxygen by hemoglobin is accompanied by the release of protons, according to the equation:

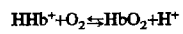

$$HHb^+ + O_2 \rightleftharpoons HbO_2 + H^+$$

Thus, an increase in the pH will pull the equilibrium to the right and cause hemoglobin to bind more oxygen at a given partial pressure. A decrease in the pH will decrease the amount of oxygen bound.

In the lungs, the partial pressure of oxygen in the air spaces is approximately 90 to 100 mm Hg and the pH is also high relative to normal blood pH (up to 7.6). Therefore, hemoglobin will tend to become almost maximally saturated with oxygen in the lungs. At that pressure and pH, hemoglobin is approximately 98 percent saturated with oxygen. On the other hand, in the capillaries in the interior of the peripheral tissues, the partial pressure of oxygen is only about 25 to 40 mm Hg and the pH is also relatively low (about 7.2 to 7.3). Because muscle cells use oxygen at a high rate thereby lowering the local concentration of oxygen, the release of some of the bound oxygen to the tissue is favored. As the blood passes through the capillaries in the muscles, oxygen will be released from the nearly saturated hemoglobin in the red blood cells into the blood plasma and thence into the muscle cells. Hemoglobin will release about a third of its bound oxygen as it passes through the muscle capillaries, so that when it leaves the muscle, it will be only about 64 percent saturated. In general, the hemoglobin in the venous blood leaving the tissue cycles between about 65 and 97 percent saturation with oxygen in its repeated circuits between the lungs and the peripheral tissues. Thus, oxygen partial pressure and pH function together to effect the release of oxygen by hemoglobin A third important factor in regulating the degree of oxygenation of hemoglobin is the allosteric effector 2,3-diphosphoglycerate (DPG). DPG is the normal physiological effector of hemoglobin in mammalian erythrocytes. DPG regulates the oxygen-binding affinity of hemoglobin in the red blood cells in relationship to the oxygen partial pressure in the lungs. In general, the higher the concentration of DPG in the cell, the lower the affinity of hemoglobin for oxygen.

When the delivery of oxygen to the tissues is chronically reduced, the concentration of DPG in the erythrocytes is increased in normal individuals. For example, at high altitudes the partial pressure of oxygen is significantly less. Correspondingly, the partial pressure of oxygen in the tissues is less. Within a few hours after a normal human subject moves to a higher altitude, the DPG level in the red blood cells increases, causing more DPG to be bound and the oxygen affinity of the hemoglobin to decrease. Increases in the DPG level of red cells also occur in patients suffering from hypoxia. This adjustment allows the hemoglobin to release its bound oxygen more readily to the tissues to compensate for the decreased oxygenation of hemoglobin in the lungs. The reverse change occurs when people acclimated to high altitudes and descend to lower altitudes.

As normally isolated from blood, hemoglobin contains a considerable amount of DPG. When hemoglobin is "stripped" of its DPG, it shows a much higher affinity for oxygen. When DPG is increased, the oxygen binding affinity of hemoglobin decreases. A physiologic allosteric effector such as DPG is therefore essential for the normal release of oxygen from hemoglobin in the tissues.

While DPG is the normal physiologic effector of hemoglobin in mammalian red blood cells, phosphorylated inositols are found to play a similar role in the erythrocytes of some birds and reptiles. Although IHP is unable to pass through the mammalian erythrocyte membrane, it is capable of combining with hemoglobin of mammalian red blood cells at the binding site of DPG to modify the allosteric conformation of hemoglobin, the effect of which is to reduce the affinity of hemoglobin for oxygen. For example, DPG can be replaced by inositol hexaphosphate (IHP), which is even more potent than DPG in reducing the oxygen affinity of hemoglobin. IHP has a 1000-fold higher affinity to hemoglobin than DPG (R.E. Benesch et at., *Biochemistry*, Vol. 16, pages 2594–2597 (1977)) and increases the $P_{50}$ of hemoglobin up to values of 96.4 mm Hg at pH 7.4, and 37 degrees C. (*J. Biol. Chem.*, Vol. 250, pages 7093–7098 (1975)).

The oxygen release capacity of mammalian red blood cells can be enhanced by introducing certain allosteric effectors of hemoglobin into erythrocytes, thereby decreasing the affinity of hemoglobin for oxygen and improving the oxygen economy of the blood. This phenomenon suggests various medical applications for treating individuals who are experiencing lowered oxygenation of their tissues due to the inadequate function of their lungs or circulatory system.

Because of the potential medical benefits to be achieved from the use of these modified erythrocytes, various techniques have been developed in the prior art to enable the encapsulation of allosteric effectors of hemoglobin in erythrocytes. Accordingly, numerous devices have been designed to assist or simplify the encapsulation procedure. The encapsulation methods known in the art include osmotic pulse (swelling) and reconstitution of cells, controlled lysis and resealing, incorporation of liposomes, and electroporation. Current methods of electroporation make the procedure commercially impractical on a scale suitable for commercial use.

The following references describe the incorporation of polyphosphates into red blood cells by the interaction of liposomes loaded with IHP: Gersonde, et al., "Modification of the Oxygen Affinity of Intracellular Haemoglobin by Incorporation of Polyphosphates into Intact Red Blood Cells and Enhanced O2 Release in the Capillary System", *Biblthca. Haemat.*, No. 46, pp. 81–92 (1980); Gersonde, et al., "Enhancement of the O2 Release Capacity and of the Bohr-Effect of Human Red Blood Cells after Incorporation of Inositol Hexaphosphate by Fusion with Effector-Containing Lipid Vesicles", *Origins of Cooperative Binding of Hemoglobin*, (1982); and Weiner, "Right Shifting of Hb-$O_2$ Dissociation in Viable Red Cells by Liposomal Technique," *Biology of the Cell*, Vol. 47, (1983).

Additionally, U.S. Pat. Nos. 4,192,869, 4,321,259, and 4,473,563 to Nicolau et at. describe a method whereby fluid-charged lipid vesicles are fused with erythrocyte membranes, depositing their contents into the red blood cells. In this manner, it is possible to transport allosteric effectors such as inositol hexaphosphate into erythrocytes, where, due to its much higher binding constant IHP replaces DPG at its binding site in hemoglobin.

In accordance with the liposome technique, IHP is dissolved in a phosphate buffer until the solution is saturated and a mixture of lipid vesicles is suspended in the solution. The suspension is then subjected to ultrasonic treatment or an injection process, and then centrifuged. The upper suspension contains small lipid vesicles containing IHP, which are then collected. Erythrocytes are added to the collected suspension and incubated, during which time the lipid vesicles containing IHP fuse with the cell membranes of the erythrocytes, thereby depositing their contents into the interior of the erythrocyte. The modified erythrocytes are then washed and added to plasma to complete the product.

The drawbacks associated with the liposomal technique include poor reproducibility of the IHP concentrations incorporated in the red blood cells and significant hemolysis of the red blood cells following treatment. Additionally, commercialization is not practical because the procedure is tedious and complicated.

In an attempt to solve the drawbacks associated with the liposomal technique, a method of lysing and the resealing red blood cells was developed. This method is described in the following publication: Nicolau, et al., "Incorporation of Allosteric Effectors of Hemoglobin in Red Blood Cells. Physiologic Effects," *Biblthca. Haemat.*, No. 51, pp. 92–107, (1985). Related U.S. Pat. Nos. 4,752,586 and 4,652,449 to Ropars et al. also describe a procedure of encapsulating substances having biological activity in human or animal erythrocytes by controlled lysis and resealing of the erythrocytes, which avoids the RBC-liposome interactions.

The technique is best characterized as a continuous flow dialysis system which functions in a manner similar to the osmotic pulse technique. Specifically, the primary compartment of at least one dialysis element is continuously supplied with an aqueous suspension of erythrocytes while the secondary compartment of the dialysis element contains an aqueous solution which is hypotonic with respect to the erythrocyte suspension. The hypotonic solution causes the erythrocytes to lyse. The erythrocyte lysate is then contacted with the biologically active substance to be incorporated into the erythrocyte. To reseal the membranes of the erythrocytes, the osmotic and/or oncotic pressure of the erythrocyte lysate is increased and the suspension of resealed erythrocytes is recovered.

In related U.S. Pat. Nos. 4,874,690 and 5,043,261 to Goodrich et al. a related technique involving lyophilization and reconstitution of red blood cells is disclosed. As part of the process of reconstituting the red blood cells, the addition of various polyanions, including inositol hexaphosphate, is described. Treatment of the red blood cells according to the process disclosed results in a cell with unaffected activity. Presumably, the IHP is incorporated into the cell during the reconstitution process, thereby maintaining the activity of the hemoglobin.

In U.S. Pat. Nos. 4,478,824 and 4,931,276 to Franco et at. a second related method and apparatus is described for introducing effective agents, including inositol hexaphosphate, into mammalian red blood cells by effectively lysing and resealing the cells. The procedure is described as the "osmotic pulse technique." In practicing the osmotic pulse technique, a supply of packed red blood cells is suspended and incubated in a solution containing a compound which readily diffuses into and out of the cells, the concentration of the compound being sufficient to cause diffusion thereof into the cells so that the contents of the cells become hypertonic. Next, a trans-membrane ionic gradient is created by diluting the solution containing the hypertonic cells with an essentially isotonic aqueous medium in the presence of at least on desired agent to be introduced, thereby causing diffusion of water into the cells with a consequent swelling and an increases in permeability of the outer membranes of the cells. This "osmotic pulse" causes the diffusion of water into the cells and a resultant swelling of the cells which increase the permeability of the outer cell membrane to the desired agent. The increase in permeability of the membrane is maintained for a period of time sufficient only to permit transport of least one agent into the cells and diffusion of the compound out of the cells.

Polyanions which may be used in practicing the osmotic pulse technique include pyrophosphate, tripolyphosphate, phosphorylated inositols, 2,3-diphosphogly-cerate (DPG), adenosine triphosphate, heparin, and polycar-boxylic acids which are water-soluble, and non-disruptive to the lipid outer bilayer membranes of red blood cells.

The osmotic pulse technique has several shortcomings including low yield of encapsulation, incomplete resealing, lose of cell content and a corresponding decrease in the life span of the cells. The technique is tedious, complicated and unsuited to automation. For these reasons, the osmotic pulse technique has had little commercial success.

Another method for encapsulating various biologically-active substances in erythrocytes is electroporation. Electroporation has been used for encapsulation of foreign molecules in different cell types including IHP red blood cells as described in Mouneimne, et al., "Stable rightward shifts of the oxyhemoglobin dissociation curve induced by encapsulation of inositol hexaphosphate in red blood cells using electroporation," FEBS, Vol. 275, No. 1, 2, pp. 117-120 (1990).

The process of electroporation involves the formation of pores in the cell membranes, or in any vesicles, by the application of electric field pulses across a liquid cell suspension containing the cells or vesicles. During the poration process, cells are suspended in a liquid media and then subjected to an electric field pulse. The medium may be electrolyte, non-electrolyte, or a mixture of electrolytes and non-electrolytes. The strength of the electric field applied to the suspension and the length of the pulse (the time that the electric field is applied to a cell suspension) varies according to the cell type. To create a pore in a cell's outer membrane, the electric field must be applied for such a length of time and at such a voltage as to create a set potential across the cell membrane for a period of time long enough to create a pore.

Four phenomenon appear to play a role in the process of electroporation. The first is the phenomenon of dielectric breakdown. Dielectric breakdown refers to the ability of a high electric field to create a small pore or hole in a cell membrane. Once a pore is created, a cell can be loaded with a biologically-active substances. The second phenomenon is the dielectric bunching effect, which refers to the mutual self attraction produced by the placement of vesicles in a uniform electric field. The third phenomenon is that of vesicle fusion. Vesicle fusion refers to the tendency of membranes of biological vesicles, which have had pores formed by dielectric breakdowns, to couple together at their mutual dialectic breakdown sites when they are in close proximity. The fourth phenomenon is the tendency of cells to line up along one of their axis in the presence of high frequency electric fields. Thus, electroporation relates to the use in vesicle rotational prealignment, vesicle bunching and dielectric constant or vesicles for the purpose of loading and unloading the cell vesicle.

Electroporation has been used effectively to incorporate allosteric effectors of hemoglobin in erythrocytes. In an article by Mouneimne, Y et al., "Stable Rightward Shifts of Oxyhemoglobin Disassociation Constant Induced by Encapsulation of Inositol Hexaphosphate in Red Blood Cells Using Electroporation", FEBS, Vol. 275, No. 1, 2, pages 11-120 (November 1990). Mouneimne and his colleagues reported that right shifts of the hemoglobin-oxygen dissociation in treated erythrocytes having incorporated IHP can be achieved. Measurements at 24 and 48 hours after loading with IHP showed a stable $P_{50}$ value indicating that resealing of the erythrocytes was permanent. Furthermore, it was shown that red blood cells loaded with inositol hexaphosphate have a normal half life of eleven days. However, the results obtained by Mouneimne and his colleagues indicate that approximately 20% of the retransfused cells were lost within the first 24 hours of transfusion.

The electroporation methods disclosed in the prior art are not suitable for processing large volumes of sample, nor use of a high or repetitive electric charge. Furthermore, the methods are not suitable for use in a continuous or "flow" electroporation chamber. Available electroporation chambers are designed for static use only. Namely, processing of samples by batch. Continuous use of a "static" chamber results in over heating of the chamber and increased cell lysis. Furthermore, the existing technology is unable to incorporate a sufficient quantity of IHP in a sufficient percentage of the cells being processed to dramatically change the oxygen carrying capacity of the blood. In addition, the prior art methods require elaborate equipment and are not suited for loading red blood cells of a patient at the point of care. Thus, the procedure is time consuming and not suitable for use on a commercial scale.

What is needed is a simple, efficient and rapid method for encapsulating biologically-active substances in erythrocytes while preserving the integrity and biologic function of the cells. The potential therapeutic applications of biologically altered blood cells suggests the need for simpler, and more effective and complete methods of encapsulation of biologically-active substances, including allosteric effectors of hemoglobin in intact erythrocytes.

There are numerous clinical conditions that would benefit from treatments that would increase tissue delivery of oxygen bound to hemoglobin. For example, the leading cause of death in the United States today is cardiovascular disease. The acute symptoms and pathology of many cardiovascular diseases, including congestive heart failure, myocardial infarction, stroke, intermittent claudication, and sickle cell anemia, result from an insufficient supply of oxygen in fluids that bathe the tissues. Likewise, the acute loss of blood following hemorrhage, traumatic injury, or surgery results in decreased oxygen supply to vital organs. Without oxygen, tissues at sites distal to the heart, and even the heart itself, cannot produce enough energy to sustain their normal functions. The result of oxygen deprivation is tissue death and organ failure.

Although the attention of the American public has long been focused on the preventive measures required to alleviate heart disease, such as exercise, appropriate dietary habits, and moderation in alcohol consumption, deaths continue to occur at an alarming rate. Since death results from oxygen deprivation, which in turn results in tissue destruction and/or organ dysfunction. One approach to alleviate the life-threatening consequences of cardiovascular disease is to increase oxygenation of tissues during acute stress. The same approach is also appropriate for persons suffering from blood loss or chronic hypoxic disorders, such as congestive heart failure.

Another condition which could benefit from an increase in the delivery of oxygen to the tissues is anemia. A significant portion of hospital patients experience anemia or a low "crit" caused by an insufficient quantity of red blood cells or hemoglobin in their blood. This leads to inadequate oxygenation of their tissues and subsequent complications. Typically, a physician can temporarily correct this condition by transfusing the patient with units of packed red blood cells.

Enhanced blood oxygenation may also reduce the number of heterologous transfusions and allow use of autologous transfusions in more case. The current method for treatment of anemia or replacement of blood loss is transfusion of whole human blood. It is estimated that three to four million patients receive transfusions in the U.S. each year for surgical or medical needs. In situations where there is more time, it is advantageous to completely avoid the use of donor or heterologous blood and instead use autologous blood.

Often the mount of blood which can be drawn and stored prior to surgery limits the use of autologous blood. Typically, a surgical patient does not have enough time to donate a sufficient quantity of blood prior to surgery. A surgeon would like to have several units of blood available. As each unit requires a period of several weeks between donations and can not be done less than two weeks prior to surgery, it is often impossible to sequester an adequate supply of blood. By processing autologous blood with IHP, less blood is required and it becomes possible to completely avoid the transfusion of heterologous blood.

As IHP-treated red cells transport 2–3 times as much oxygen as untreated red cells, in many cases, a physician will need to transfuse fewer units of IHP-treaded red cells. This exposes the patient to less heterologous blood, decreases the extent of exposure to viral diseases from blood donors and minimizes immune function disturbances secondary to transfusions. The ability to infuse more efficient red blood cells is also advantageous when the patients blood volume is excessive. In other more severe cases, where oxygen transport is failing, the ability to rapidly improve a patient's tissue oxygenation is life saving.

Although it is evident that methods of enhancing oxygen delivery to tissues have potential medical applications, currently there are no methods clinically available for increasing tissue delivery of oxygen bound to hemoglobin. Transient, 6 to 12 hour elevations of oxygen deposition have been described in experimental animals using either DPG or molecules that are precursors of DPG. The natural regulation of DPG synthesis in vivo and its relatively short biological half-life, however, limit the DPG concentration and the duration of increased tissue $PO_2$, and thus limit its therapeutic usefulness.

What is needed is a simple, efficient and rapid method for encapsulating biologically-active substances, such as IHP, in erythrocytes without damaging the erythrocytes.

SUMMARY OF THE INVENTION

The present invention relates to a method and apparatus for the encapsulation of biologically-active substances in various cell populations. More specifically, the present invention provides an electroporation chamber that may form part of an automated, self-contained, flow apparatus for encapsulating compounds or compositions, such as inositol hexaphosphate, in red blood cells, thereby reducing the affinity of the hemoglobin for oxygen and enhancing the delivery of oxygen by red blood cells to tissues. Encapsulation is preferably achieved by electroporation; however, it is contemplated that other methods of encapsulation may be used in practicing the present invention. The method and apparatus, including the electroporation chamber, of the present invention, is equally suited to the encapsulation of a variety of biologically-active substances in various cell populations.

The apparatus and method of the present invention is suited to the incorporation of a variety of biologically-active substances in cells and lipid vesicles. The method, apparatus and chamber of the present invention may be used for introducing a compound or biologically-active substance into a vesicle whether that vesicle is engineered or naturally occurring. For example, the apparatus, method, and chamber of the present invention may be used to introduce IHP into erythrocytes.

The encapsulation of inositol hexaphosphate in red blood cells by electroporation according to the present invention results in a significant decrease in the hemoglobin affinity for oxygen without affecting the life span, ATP levels, K+ levels, or normal rheological competence of the cells. In addition, the Bohr effect is not altered except to shift the $O_2$ binding curve to the right. Lowering the oxygen affinity of the erythrocytes increases the capacity of erythrocytes to dissociate the bound oxygen and thereby improves the oxygen supply to the tissues. Enhancement of the oxygen-release capacity of erythrocytes brings about significant physiological effects such as a reduction in cardiac output, an increase in the arteriovenous differences, and improved tissue oxygenation.

The modified erythrocytes prepared in accordance with the present invention, having improved oxygen release capacities, may find their use in situations such as those illustrated below:

1. Under conditions of low oxygen-partial pressure, such as at high altitudes;
2. When the oxygen exchange surface of the lung is reduced, such as occurs in emphysema;
3. When there is an increased resistance to oxygen diffusion in the lung, such as occurs in pneumonia or asthma;
4. When there is a decrease in the oxygen-transport capacity of erythrocytes, such as occurs with erythropenia or anemia, or when an arteriovenous shunt is used;
5. To treat blood circulation disturbances, such as arteriosclerosis, thromboembolic processes, organ infarct, congestive heart failure, cardiac insufficiency or ischemia;
6. To treat conditions of high, oxygen affinity of hemoglobin, such as hemoglobin mutations, chemical modifications of N-terminal amino acids in the hemoglobin-chains, or enzyme defects in erythrocytes;
7. To accelerate detoxification processes by improving oxygen supply;
8. To decrease the oxygen affinity of conserved blood; or
9. To improve the efficacy of various cancer treatments.

According to the method and apparatus of the present invention, it is possible to produce modified erythrocytes which contribute to an improved oxygen economy of the blood. These modified erythrocytes are obtained by incorporation of allosteric effectors, such as IHP, by electroporation of the erythrocyte membranes.

The incorporation of the biologically-active substances into the cells in accordance with the method of the present invention, including the encapsulation of allosteric effectors of hemoglobin into erythrocytes, is conducted extracorporally via an automated, flow electroporation apparatus.

Briefly, a cell suspension is introduced into the separation and wash bowl chamber of the flow encapsulation apparatus. The cells are separated from the suspension, washed and resuspended in a solution of the biologically-active substance to be introduced into the cell. This suspension is introduced into the electroporation chamber and then incubated. Following electroporation and incubation, the cells are washed and separated. A contamination check is optionally conducted to confirm that all unencapsulated biologically-active substance has been removed. Then, the cells are prepared for storage or reintroduction into a patient.

In accordance with the present invention and with reference to the preferred embodiment, blood is drawn from a patient, the erythrocytes are separated from the drawn blood, the erythrocytes are modified by the incorporation of allosteric effectors and the modified erythrocytes and blood plasma is reconstituted. In this manner, it is possible to prepare and store blood containing IHP-modified erythrocytes.

The apparatus of the present invention provides an improved method for the encapsulation of biologically-active substances in cells including an apparatus which is self-contained and therefore sterile, an apparatus which can process large volumes of cells within a shortened time period, an apparatus having improved contamination detection, cooling and incubation elements, an apparatus is entirely automated and which does not require the active control of a technician once a sample is introduced into the apparatus.

Thus, it is an object of the present invention to provide an automated, continuous flow encapsulation apparatus.

It is a further object of the present invention to provide an automated, continuous flow electroporation apparatus.

It is a further object of the present invention to provide a continuous flow encapsulation apparatus which produces a homogenous population of loaded cells or vesicles.

It is another object of the present invention to provide a continuous flow electroporation device which produces a homogenous population of loaded cells or vesicles.

It is another object of the present invention to provide a sterile and nonpyrogenic method of encapsulating biologically-active substances in cells.

It is another object of the present invention to provided a method and apparatus which results in stable resealing of cells or vesicles following electroporation to minimize lysis of the modified cells or vesicles after electroporation.

It is another object of the present invention to provide a flow encapsulation apparatus which produces a modified cell population from which all exogenous non-encapsulated biologically-active substances have been removed.

It is another object of the present invention to provide an electroporation apparatus which produces a modified cell population from which all exogenous, non-encapsulated biologically-active substances have been removed.

It is another object of the present invention to provide a method and apparatus that allows continuous encapsulation of biologically-active substances in a population of cells or vesicles.

It is a further object of the present invention to provide a method and apparatus that achieves the above-defined objects, features, and advantages in a single cycle.

It is another object of the present invention to provide a continuous flow electroporation chamber.

It is another object of the present invention to provide an improved and more efficient method of encapsulating biologically active substances in cells than those methods currently available.

It is a further object of the present invention to provide a composition suitable for use in the treatment of conditions and/or disease states resulting from a lack of or decrease in oxygenation.

Other objects, features, and advantages of the present invention will become apparent upon reading the following detailed description of the preferred embodiment of the invention when taken in conjunction with the drawings and the appended claims.

BRIEF DESCRIPTION OF THE DRAWINGS

FIG. 1 is a schematic diagram of a first embodiment of a continuous flow encapsulation apparatus.

FIG. 2 is a schematic diagram of a second embodiment of a continuous flow encapsulation apparatus.

FIG. 3 is a top view of a first embodiment of the flow electroporation chamber with electrodes.

FIG. 4 is a top view of a first embodiment of the flow electroporation chamber without electrodes.

FIG. 5 is a side view of a first embodiment of the flow electroporation chamber.

FIG. 6 is an end view of a first embodiment of the flow electroporation chamber.

FIG. 9 is an exploded perspective view of a second embodiment of the flow electroporation chamber.

FIG. 10 is a perspective view of the flow electroporation chamber of FIG. 9 with the chamber being assembled.

FIG. 14 is a front elevation view of a support member of an electroporation chamber according to a third embodiment of the present invention.

FIG. 15 is a cross-sectional view of the support member of FIG. 14 taken along line 15—15 of FIG. 14.

FIG. 16 is an enlarged view of the section indicated by the circle 16 of FIG. 15.

FIG. 17 is an exploded perspective view of the electroporation chamber according to the third embodiment and support column to which the chamber is mounted.

FIG. 18 is a perspective view showing the electroporation chamber of FIG. 17 mounted to the support column.

FIG. 20 is a perspective cut-away view of the electroporation chamber and support column of FIG. 19.

FIG. 21 is a schematic view of a self-contained electroporation apparatus comprising the electroporation chamber of FIGS. 14–20.

DETAILED DESCRIPTION OF THE INVENTION

Figure 7:
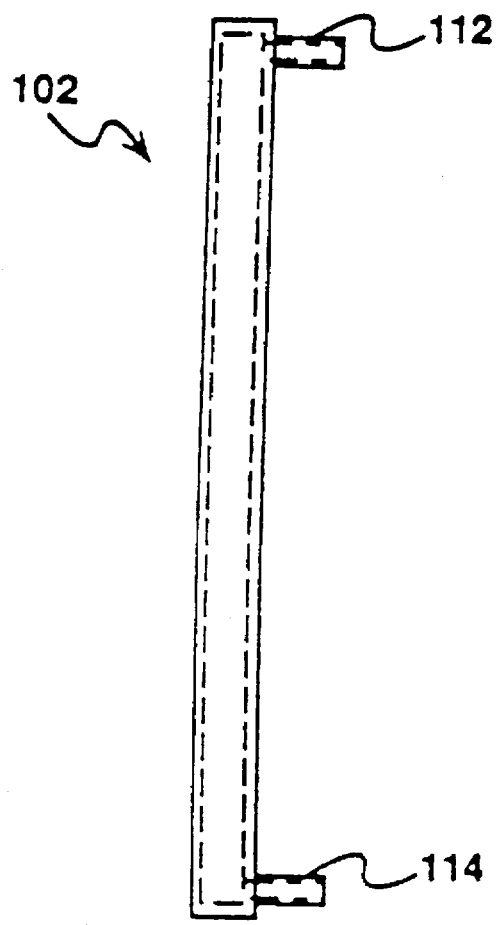
FIG. 7 is a side view of an electrode for use with the first embodiment of the flow electroporation chamber.

The present invention provides an automated, self-contained, flow apparatus for encapsulating allosteric compounds or compositions, such as inositol hexaphosphate, in cells, such as red blood cells. In one embodiment, the apparatus of the present invention combines the features of a plasmaphoresis apparatus with those of a flow electroporation apparatus to form an automated, self-contained flow electroporation device. The present invention further comprises a new flow electroporation chamber that allows use of the chamber under flow rather than static conditions. It is contemplated that the method and apparatus, including the electroporation chamber of the present invention, may be used to encapsulate a variety of biologically-active substances in diverse cell populations.

Additionally, the present invention provides a population of modified cells having physical characteristics that make the cells particularly useful for treating conditions which demand or benefit from an increase in the delivery of oxygen to the tissues. In accordance with the method of the present invention, a homogenous population of IHP loaded red blood cells can be obtained with reduced contamination and a reduced propensity to lyse following encapsulation. The treated red blood cells exhibit normal life spans in circulation. Using the present invention, red blood cells of a patient in need of the treatment can be quickly loaded and returned to the patient's circulation.

Related International Application No. PCT/US 94/03 189, filed Mar. 23, 1994, which is a continuation-in-part of U.S. application Ser. No. 035,467, filed Mar. 23, 1993, are hereby incorporated by reference.

The method of operation of the apparatus of the present invention is described below with reference to the preferred use of the apparatus, i.e., the encapsulation of allosteric effectors of hemoglobin in red blood cells. Inositol hexaphosphate is the preferred allosteric effector to be used with the present invention. Other sugar phosphates, such as inositol pentaphosphate, inositol tetraphosphate, inositol triphosphate, inositol diphosphate and diphosphatidyl inositol diphosphate, can also be used. Other suitable allosteric effectors include polyphosphates such as nucleotide triphosphates, nucleotide diphosphates, nucleotide monophosphates, and alcohol phosphate esters. In case of certain mutations of hemoglobin, e.g. "Zurich" hemoglobin, organic anions such as polycarboxylic acids can be used as allosteric effectors. Finally, it is possible to use inorganic anions such as hexacyano ferrate, phosphate or chloride as allosteric effectors.

Red blood cells that have been loaded with inositol hexaphosphate according to the present invention can be used to treat a wide variety of diseases and disease states. The IHP loaded red blood cells made according to the present invention can be administered to a patient undergoing a heart attack thereby increasing the oxygen delivery to the ischemic heart tissue and, at the same time, reducing the cardiac output. The IHP-loaded red blood cells made according to the present invention also can be used to treat any ischemic condition including, but not limited to, "bleeding" anemia, surgicial complications, stroke, diabetes, sickle cell disease, burns, intermittent claudication, emphysema, hypothermia, peripheral vascular disease, congestive heart failure, angina, transient ischemic disease, disseminated intravascular coagulation, adult respiratory distress syndrome (ARDS) and cystic fibrosis. A detailed description of the medical applications of compositions prepared in accordance with the method of the present invention is also provided below.

Continuous Flow Encapsulation Apparatus

The method of operation of the apparatus of the present invention is described below with reference to the preferred use of the apparatus, i.e., the encapsulation of allosteric effectors of hemoglobin in red blood cells by electroporation. It is to be understood that the apparatus may be adapted to accommodate other cell populations or vesicles, and other biologically active substances. Additionally, the apparatus maybe adapted to utilize methods of encapsulation other than electroporation.

Briefly, in accordance with the present invention, a sample of blood is introduced into the continuous flow encapsulation apparatus. If red blood cells are being collected, the blood can either be drawn directly from a patient or can be previously drawn blood. The blood is initially separated into red blood cells, plasma and white blood cells, and waste products. The waste products include the diluent and various blood solutes remaining in the supernatant after centrifugation. They are stored in a waste reservoir within the apparatus. The blood plasma and white blood cells are also retained in a reservoir within the system while the red blood cells are admixed with the substance to be encapsulated. The suspension of red blood cells is then subjected to electroporation. Following electroporation, the red blood cells are incubated under conditions which allow the cells to reseat. They are then processed and washed to eliminate exogenous, non-encapsulated biologically-active substances. When the cells have been processed, the red blood cells containing the encapsulated substances can be optionally reconstituted with the blood plasma and white blood cells. The reconstituted blood may then be returned directly to the patient or can be stored for later use. Although described as discrete steps, the process is essentially continuous.

A first embodiment of the present invention is described with reference to FIG. 1, which schematically illustrates the structure of the continuous flow encapsulation apparatus of the present invention.

In accordance with the present invention, a volume of whole blood is admitted into the electroporation system 5 at input 11. The blood sample may optionally be drawn directly from a patient into the electroporation system 5, or the blood may be drawn at an earlier time and stored prior to introduction into the system 5. Valve 12 is opened to admit the sample into the system 5. Simultaneously, valve 25 is opened and pump 22 is engaged to admit an anti-coagulant from the anti-coagulant reservoir 27. A suitable anticoagulant is heparin, although other anticoagulants can be used. The preferred anticoagulant is ACD. Valves 15 and 36 are also opened and pump 40 is engaged. The admixture of anticoagulant and whole blood passes through a filter 18 and a pressure evaluation system 19 that monitors the flow through the apparatus, and is collected in a blood separation and wash bowl 44 which is activated when pump 40 is engaged. A sensor indicates when the blood separation and wash bowl 44 has been filled with red blood cells. When it has been filled, the blood supply is stopped. The steps involving separation of the blood components can be accomplished by a plasmaphoresis apparatus, such as the plasmaphoresis apparatus manufactured by Haemonetics Corporation (Haemonetics Corporation, Braintree, Mass.).

As explained above, when pump 40 is engaged in a clockwise direction, the blood separation and wash bowl 44 is engaged and the anti-coagulant and whole blood suspension is centrifuged to separate the plasma, white blood cells, red blood cells, and waste. Valve 87 is opened to admit the plasma and white blood cells into the plasma reservoir 89.

Optionally, and dependent on the cell population being processed by the apparatus, the cells retained in the blood separation and wash bowl 44 are then washed. Valves 33, 15, and 36 are opened to admit saline buffer from the diluent reservoir 30 into the blood separation and wash bowl 44 which contains the red blood cells. Pump 40 is still engaged. The red blood cells are then washed and centrifuged. The preferred saline buffer is a 0.9% sodium chloride solution, although other physiologically isotonic buffers can be used to dilute and wash the red blood cells. Valve 54 is opened to admit the waste into the waste reservoir 57 during the washing process. Again, the waste is stored in the waste reservoir 57 and the red blood cells are retained in the blood separation and wash bowl 44. The wash process is repeated if necessary.

It has been found through experiments conducted with a variety of changes in pulse lengths and field strengths that square pulses result in less-efficient encapsulation of IHP into human erythrocytes. The creation of large pores in the cell membrane appears to be insufficient for the entry of extracellular IHP into red blood cells. This suggests a more complex process than the diffusion of IHP into the cells after the creation of the pores. It is proposed that the electrical pulse has to accomplish two tasks. The first is the generation of pores in the cell membrane and the second is the active electrophoretic movement of the IHP through those pores into the red blood cell. This can be accomplished through the use of high voltage square pulses (2.13 kV/cm, 2 ms) immediately followed by a lower voltage exponential pulse (1.5 to 1.75 kV/cm, 5 ms), which leads to an increased encapsulation of IHP into red blood cells of up to 50% of the usual expontential pulse protocol encapsulation. The expontential pulse itself is well below the electroporation threshold. Both tasks, namely pore formation and electrophoretic movement, can be most effectively accomplished with use of exponetial pulses.

Following separation of the red blood cells, pump 40 is reversed, pump 22 is turned off, valves 12, 15, 33, 36, 25, 87, and 54 are closed, and valves 97 and 64 are opened. The IHP solution is pumped out of the IHP reservoir 50 while, simultaneously, red blood cells are pumped out of the blood separation and wash bowl 44 towards the cooling coil 68. The red blood cells and IHP solution are admixed in the tubing of the apparatus at junction 67 and then pumped through the cooling coil 68. In a preferred embodiment of the present invention, and as explained in detail below, the IHP solution and red blood cells may be admixed in the separation and wash bowl 44 before being admired into the cooling coil 68.

The preferred concentration of IHP in the solution is between approximately 10 mMol and 100 mMol with a more preferred concentration of approximately 23 to 35 mMol, and a most preferred concentration of 35 mMol. The preferred IHP solution comprises the following compounds, in the following concentrations:

35 mMol IHP salt neutralized with 35 mMol IHP acid to a pH of 7.3
33 mMol $K_2HPO_4$
7.0 mMol $NaH_2$
30.6 mMol KCL
6.4 mMol NaCl
7.3 mMol Sucrose
5.0 mMol ATP A second IHP solution for use with the present invention comprises the following compounds, in the following concentrations:

23 mMol IHP salt neutralized with HCl to a pH of 7.3
40 mMol $K_2HPO_4$
7 mMol $NaH_2$ The IHP may be obtained from Sigma Chemical Company of St. Louis, Miss.

The hematocrit of the suspension is preferably between approximately 30 and 80 with the most preferred hematocrit of approximately 50. Pump 40 is designed to pump both red blood cells and IHP solution and can be adjusted so that the final hematocrit entering the cooling coil 68 can be predetermined.

After mixing, the red blood cell-IHP suspension is then pumped through a cooling coil 68. Cooling can be achieved with a water bath or with a thermo-electric based cooling system. For example, cooling coil 68 is immersed in a cooling bath in the cooling reservoir 69. When the red blood cell-IHP suspension passes through the cooling coil 68, the suspension is cooled to a temperature of between approximately 1° C. and 12° C., preferably approximately 4° C. Cooling the red blood cells ensures the survival of the pore created in the cell membrane during the electroporation process. The use of a cooling coil aids in the speed of cooling by increasing the surface area of the sample in contact with the cooling element. Optionally, the cooling coil can be surrounded by a thermo-electric heat pump.

Certain applications may require heating of the cell suspension prior to electroporation. In such a case, a heating coil may replace the cooling coil 68. The maximum temperature tolerated by red blood cells is approximately 37° C.

A thermoelectric heat pump works by extracting thermal energy from a particular region, thereby reducing its temperature, and then rejecting the thermal energy into a "heat sink" region of higher temperature. At the cold junction, energy is absorbed by electrons as they pass from a low energy level in the p-type semiconductor element, to a higher energy level in the n-type semiconductor element. The power supply provides the energy to move the electrons through the system. At the hot junction, energy is expelled into a heat sink as electrons move from a high energy level element (n-type) to a lower energy level element (p-type).

Thermoelectric elements are totally solid state and do not have moving mechanical parts or require a working fluid, as do vapor-cycle devices. However, thermoelectric heat pumps perform the same cooling functions as freon-based vapor compression or absorption refrigerators. Thermoelectric heat pumps are highly reliable, small in size and capacity, low cost, low weight, intrinsically safer than many other cooling devices, and are capable of precise temperature control.

The preferred thermoelectric heat pumps for use in the present invention are manufactured by MELCOR Materials Electronic Products Corp. of Trenton, N.J. The thermocouples are made of high performance crystalline semiconductor material. The semiconductor material is bismuth telluride, a quaternary alloy of bismuth, tellurium, selenium, and antimony, doped and processed to yield oriented polycrystalline semiconductors with properties. The couples, connected in series electrically and in parallel thermally, are integrated into modules. The modules are packaged between metallized ceramic plates to afford optimum electrical insulation and thermal conduction with high mechanical strength in compression. Modules can be mounted in parallel to increase the heat transfer effect or can be stacked in multiple-stage cascades to achieve high differential temperatures. Passing a current through the heat pump generates a temperature differential across the thermocouples, with maximum ratings of 70° C. and higher.

After cooling, the red blood cell-IHP suspension enters the electroporation chamber 72 where an electric pulse is administered from a pulse generator 75 to the red blood cell-IHP suspension, causing openings to form within the cell membranes of the red blood cells. Optionally, an automatic detection system will turn the pulse generator 75 on when the chamber 72 is filled with red blood cell-IHP suspension. An electrical pulse is applied to the suspension every time the chamber 72 is filled with unencapsulated cells. A conventional electroporation chamber may be used when the operation of the apparatus is static, namely, when single discrete batches of cells are processed. In a preferred embodiment of the present invention a flow electroporation chamber is used. In one embodiment, a flow electroporation chamber 72 is constructed of clear polyvinyl chloride, and contains two opposing electrodes spaced a distance of 7 mm apart. The distance between the electrodes will vary depending on the flow volume and field strength. Preferably, the flow electroporation chamber 72 is disposable. The electroporation chamber may also be constructed of polysolfone, which is preferably for use with certain sterilization procedures, such as autoclaving. A detailed description of the structure and construction of the flow electroporation chamber is provided below.

The red blood cell-IHP suspension passes between the two electrodes of the electroporation chamber 72. When a suspension of non-treated cells enter the chamber 72, an electrical field of 1 to 3 KV/cm is created and maintained for a period of 1 to 4 milliseconds, preferably for a period of 2 milliseconds with a 1.8 ml flow chamber. Preferably, the IHP-red blood cell suspension is subjected to three high voltage pulses per volume at a fieldstrength of approximately 2600 to 3200 V/cm per pulse. The pulse of current across the cell membranes causes an electrical breakdown of the cell membranes, which creates pores in the membranes. IHP then diffuses into the cell through these pores.

Following electroporation, the red blood cell-IHP suspension enters an incubation chamber 78 where the suspension is incubated at room temperature for an incubation time of between approximately 15 minutes and 120 minutes with the preferred incubation time of 30 to 60 minutes. Optionally, the red blood cell-IHP suspension is incubated for approximately 5 minutes at a temperature of approximately 37° C., and at least 15 minutes at room temperature. The incubation chamber 78 may optionally be surrounded by a heating means 80. For example, the heating means 80 can be a water bath or can be a thermoelectric heat pump.

Optionally, the incubator 78 contains a resealing buffer which aids in resealing and reconstitution of the red blood cells. The preferred composition of the resealing buffer is provided below:

| RESEALING BUFFER | |
|---|---|
| I. Combine | |
| Sodium chloride | 150 mMol |
| Potassium chloride | 8 mMol |
| Sodium phosphate | 6 mMol |
| Magnesium sulfate | 2 mMol |
| Glucose | 10 mMol |
| Adenine | 1 mMol |
| Inosine | 1 mMol |
| Penicillin G | 500 units/ml |
| Chloramphenicol | 0.1 mg/ml |
| II. Add | |
| BSA | 3.5% |
| Calcium chloride | 2 mMol |

In the preferred embodiment of the present invention, no resealing buffer is used.

Following incubation, valve 51 is opened and pump 40 is engaged and the red blood cell-IHP suspension is returned to the blood separation and wash bowl 44 from the incubation chamber 78. The excess IHP solution is removed from the red blood cell suspension by centrifugation. The waste IHP solution is directed to waste reservoir 57. Valves 33, 15 and 36 are then opened to admit a volume of diluent into the blood separation and wash bowl 44. The red blood cell-IHP suspension is then centrifuged and the supernatant is discarded in the waste reservoir 57 through valve 54 leaving the red blood cells in the blood separation and wash bowl 44. A saline buffer is added to the modified red blood cells from the diluent reservoir 30. The cells are washed and the supernatant is discarded following centrifugation. The wash process is repeated if needed.

Optionally, as the waste is removed from the separation and wash bowl 44 it passes through a contamination detector 46 to detect any free IHP in the waste solution thereby confirming that exogenous non-encapsulated IHP has been removed from the modified red blood cells. The contamination detection system relies on optical changes in the washing buffer. After the modified red blood cells have been washed and centrifuged, the supernatant passes through the contamination detector 46 before it is deposited in the waste reservoir 57. If exogenous, non-encapsulated IHP remains in the washing buffer, the discarded solution will be turbid. The turbidity is due to the reaction of IHP with calcium, which is a component of the wash buffer. The contamination detector 46 uses an optical detection system. Preferably, the light source is an LED and the detector is a photodiode. The voltage difference of the photodiode will indicate the amount of IHP in the wash solution. The contamination detector 46 is optional.

Following washing, the IHP-red blood cell product is optionally reconstituted with the plasma and white blood cells which had been retained in reservoir 89. The treated red blood cells may be collected in a reinjection bag, either in a preservation media or in the autologous plasma of the patient.

The IHP-loaded red blood cells obtained can be administered directly back into the patient or the cells can be stored for later use. The IHP in the red blood cells is not released during the normal storage time.

A preferred embodiment of the present invention is described with reference to FIG. 2, which schematically illustrates the structure of the continuous flow encapsulation apparatus of the present invention. Again, the method of operation of the apparatus is described with reference to the preferred use of the apparatus, i.e., the encapsulation of allosteric effectors of hemoglobin in red blood cells by electroporation. It is to be understood that the apparatus may be adapted to accommodate other cell populations or vesicles, and other biologically active substances. Additionally, the apparatus maybe adapted to include other methods of encapsulation.

In accordance with the present invention, a sample of whole blood is admitted into the electroporation system 10 at input 11. Valve 12 is opened to admit the sample into the system 10. Simultaneously, valve 25 is opened and pump 22 is engaged to admit an anti-coagulant from the anti-coagulant reservoir 27. Valves 15 and 36 are also opened and pump 40 is engaged.

The admixture of anticoagulant and whole blood passes through a filter 18 and a pressure evaluation system 19, and is collected in a blood separation and wash bowl 44 which is activated when pump 40 is engaged. A sensor indicates when the blood separation and wash bowl 44 has been filled with red blood cells.

When pump 40 is engaged in a clockwise direction, the blood separation and wash bowl 44 is engaged and the anti-coagulant and whole blood suspension is centrifuged to separate the plasma, white blood cells, red blood cells, and waste. Valve 87 is opened to admit the plasma and white blood cells into the plasma reservoir 89.

Optionally, the cells retained in the separation and wash bowl 44 are then washed and centrifuged. Valves 33, 35, 15, and 36 are opened to admit saline buffer from the diluent reservoir 30 into the blood separation and wash bowl 44 which contains the red blood cells. Valve 12 is closed and pump 40 remains engaged.

During washing, valve 54 is opened to admit the waste into the waste reservoir 57 during the washing process. Again, the waste is stored in the waste reservoir 57 and the red blood cells are retained in the blood separation and wash bowl 44. The wash process is repeated if necessary. A contamination detection system may optionally be installed between the separation and wash bowl 44 and the waste reservoir 57 to control the wash process.

Following separation of the red blood cells, pump 40 is reversed, pump 22 is turned off, valves 12, 15, 33, 35, 36, 25, 87, and 54 are closed, and valve 97 is opened. If the cells were washed, pump 22 was previously turned off and valves 12 and 25 had been closed. The IHP solution is pumped out of the IHP reservoir 50 and into the separation and wash bowl 44 containing the red blood cells. There, the red blood cells and IHP are admixed to form a suspension.

The preferred concentration of IHP in the solution is between approximately 10 mMol and 100 mMol with a more preferred concentration of approximately 23 to 35 mMol, and with a most preferred concentration of 35 mMol. The preferred IHP solution comprises the following compounds, in the following concentrations:

35 mMol IHP salt neutralized with 35 mMol IHP acid to a pH of 7.3
33 mMol $K_2HPO_4$
7 mMol NaH2
30.6 mMol KCL
6.4 mMol NaCl
7.3 mMol Sucrose
5.0 mMol ATP The IHP may be obtained from Sigma Chemical Company of St. Louis, Miss.

The hematocrit of the suspension is preferably between approximately 30 and 60 with the most preferred hematocrit of approximately 50. Pump 40 is designed to pump both red blood cells and IHP solution and can be adjusted so that the final hematocrit entering the cooling coil 68 can be predetermined. The steps of collecting the specimen, separating the cells from the specimen, washing the cells, and combining the cells with IHP can be done with an apheresis-blood washing machine, such as that manufactured by Haemonetics corporation. The apheresis-blood washing machine is coupled to the flow electrophoresis apparatus described herein to form a continuous flow electroporation apparatus.

After combining the red blood cells with the IHP solution, pump 40 is again reversed, valve 97 is closed and valve 64 is opened. The red blood cell-IHP suspension is then pumped through a thermoelectric cooling coil 68. A blood bag from a blood warming set, such as the blood bag provided in the Fenwal® Blood Warming Set manufactured by Baxter Healthcare Corporation can be used as the cooling coil 68. When the red blood cell-IHP suspension passes through the cooling coil 68 in the cooling reservoir 69, the suspension is cooled to a temperature of between approximately 1° C. and 12° C., preferably approximately 4° C. Optionally, a pump may be added to the apparatus between the cooling coil 68 and cooling reservoir 69, and the electroporation chamber 72, to ensure a constant flow rate and compensate for fluctuation in volume that occurs when the cooling coil 68 is filled.

Optionally, the pre-cooling step may be eliminated and the red blood cell-IHP suspension may be directed to the electroporation chamber 72 immediately after admixing. In such an instance, the cooling coil 68 and cooling reservoir 69 would be eliminated from the continuous flow encapsulation apparatus 10. Cooling prior to electroporation may not be required if the temperature of the electroporation chamber is sufficiently cool to maintain the cells suspension at 4° C.

After cooling, the red blood cell-IHP suspension enters the electroporation chamber 72. The chamber 72 is maintained at a temperature of approximately 4° C. As the red blood cell-IHP suspension passes through the flow electroporation chamber 72, an electric pulse is administered from a pulse generator 75 to the suspension causing openings to form within the cell membranes of the red blood cells.

The red blood cell-IHP suspension passes between two electrodes of the electroporation chamber 72. FIGS. 3 to 10 describe the electroporation chamber. In a preferred embodiment of the present invention, when a suspension of non-treated cells enters the chamber 72, the IHP-red blood cell suspension is subjected to approximately three high voltage pulses per volume at a fieldstrength of approximately 2600 to 3200 V/cm per pulse. The charge created across the cell membranes causes an electrical breakdown of the cell membrane, which creates pores in the membrane. IHP then diffuses into the cell through these pores.

During electroporation, an electrical field of 1 to 3 KV/cm is created and maintained for a period of 1 to 4 milliseconds. The preferred pulse length is 3 to 4 milliseconds, with a most preferred pulse length of 2 milliseconds. Pulse length is defined as 1/e. At a flow rate of approximately 10.6 ml/minute, the preferred number of pulses is 3, at the preferred pulse rate of 0.29 Hz. The fieldstrength is defined as the voltage over the distance between the electrodes. The distance between electrodes is measured in centimeters. The preferred electrical parameters are as follows:

Exponential Pulse:
 pulse length=1.5 to 2.5 ms
 fieldstrength=2.7 to 3 KV/cm

Following electroporation, the red blood cell-IHP suspension enters an incubation chamber 78 where the suspension is incubated at room temperature for an incubation time of between approximately 10 minutes and 120 minutes with a preferred incubation time of 30 minutes. Optionally, the red blood cell-IHP suspension is incubated for approximately 5 minutes at a temperature of approximately 37° C., and at least 15 minutes at room temperature. The incubation chamber 78 may be surrounded by a heating means 80. Any heating means 80 can be used in practicing the present invention. The preferred heating means 80 are a water bath or a thermoelectric heat pump.

Optionally, the incubator 78 contains a resealing buffer which aids in resealing and reconstitution of the red blood cells. In the preferred embodiment of the present invention, no resealing buffer is used.

Following incubation, the red blood cell-IHP suspension is returned to the blood separation and wash bowl 44 when valve 51 is opened and pump 40 is engaged. The excess IHP solution is removed from the red blood cell suspension by centrifugation. The waste IHP solution is directed to waste reservoir 57. Valves 33, 37, 15 and 36 are then opened to admit a volume of post wash solution from reservoir 31 into the blood separation and wash bowl 44. In a preferred embodiment of the present invention, the post wash solution comprises a 0.9% NaCl₂ solution, including 2.0 mM CaCl₂ and 2.0 mM MgCl₂. Any physiological saline may be used.

After addition of the post wash solution, the red blood cell-IHP suspension is then centrifuged and the supernatant is discarded in the waste reservoir 57 through valve 54 leaving the red blood cells in the blood separation and wash bowl 44. The wash process is repeated until all unencapsulated IHP has been removed.

Optionally, as the waste is removed from the separation and wash bowl 44 it passes through a contamination detector 46 to detect any free IHP in the waste solution thereby confirming that exogenous non-encapsulated IHP has been removed from the modified red blood cells. The contamination detector 46 is optional.

Following washing, the red blood cells containing IHP may be reconstituted with the plasma and white blood cells retained in reservoir 89. Pump 40 is engaged and valves 87, 36, and 92 are opened. The modified red blood cells and plasma and white blood cells are pumped to reservoir 96. A filter may be installed between reservoir 96 and valve 92 to remove any aggregates or other impurities from the reconstituted modified blood.

The IHP-loaded red blood cells obtained in accordance with the method of the present invention can be administered directly back into the patient or the cells can be stored for later use. The IHP in the red blood cells is not released during the normal storage time.

It is contemplated that continuous flow encapsulation apparatus of the present invention may be modified to utilize other encapsulation methods.

Furthermore, it is contemplated that the continuous flow encapsulation apparatus may be adapted to process various diverse cell populations. Furthermore, the apparatus may be used to encapsulate biologically active substances in artificial vesicles.

It is also contemplated that the continuous flow encapsulation apparatus of the present invention may be used to encapsulate a broad range of biologically active substances.

The flow electroporation apparatus of the present invention may be separated from the plasmaphoresis apparatus of the present invention. The blood cooling system, peristaltic pump, electroporation chamber, pulse generator, and electronics comprising the flow electroporation apparatus may be linked to a plasmaphoresis apparatus and interface with the controls of that machine.

While this invention has been described in specific detail with reference to the disclosed embodiments, it will be understood that many variations and modifications may be effected within the spirit and scope of the invention as described in the appended claims.

Flow Electroporation Chamber

During electroporation, the insertion rate of IHP is linearly dependent on the voltage administered to the cells. Generally, the higher the voltage, the more IHP is encapsulated; however, cell lysis is also increased and cell survival is decreased. The efficiency of an electroporation system may be judged by cell survival after electroporation. Poor cell survival indicates very low efficiency. The amplitude and duration of the electrical pulse is responsible for the electric breakdown of the cell membrane and creates pores in the pole caps parallel to the electric field. Thus, the factors to be considered in designing an electroporation system include the field strength, the pulse length and the number of pulses.

A perfect electroporation target is shaped like a sphere, so its orientation does not effect the efficiency of the applied field. When the target is spherical, a single pulse with a fieldstrength above the threshold can electroplate 100% of the target. Red blood cells are disk shaped. Because of their shape and orientation in the electroporation chamber, only approximately 40% of the cells are electroplated during a single pulse. To also electroporate the other 60%, the fieldstrength can be increased. This increases the stress on the red blood cells in proper orientation to the electric field and leads to lower survival rates of the cells.

To achieve more efficient encapsulation while reducing the incidence of cell lysis and death, a flow electroporation chamber utilizing short duration multiple pulses was developed. With the flow-through rate steady and a steady field voltage, it was determined that plurality of pulses would insert maximal quantities of IHP with minimal 2 to 24 hour all lysis. A multiple-pulse system allows an increase in the cell survival rate without increasing the field strength. When a multiple-pulse system is used, orientation of the cells is not as critical as it is when a system is a single pulse system is used. The lower fieldstrength is much more gentle to the red blood cells. It is much easier to electroporate every single cell in the multiple pulse system, because the timing between the flow rate of the red blood cells through the chamber and the electroporation pulses, and the orientation of the cells is not as crucial as in a single pulse system. The flow multiple-pulse electroporation system also increases both the short term and the long term survival of red blood cells when compared to the single pulse method.

Figure 11:
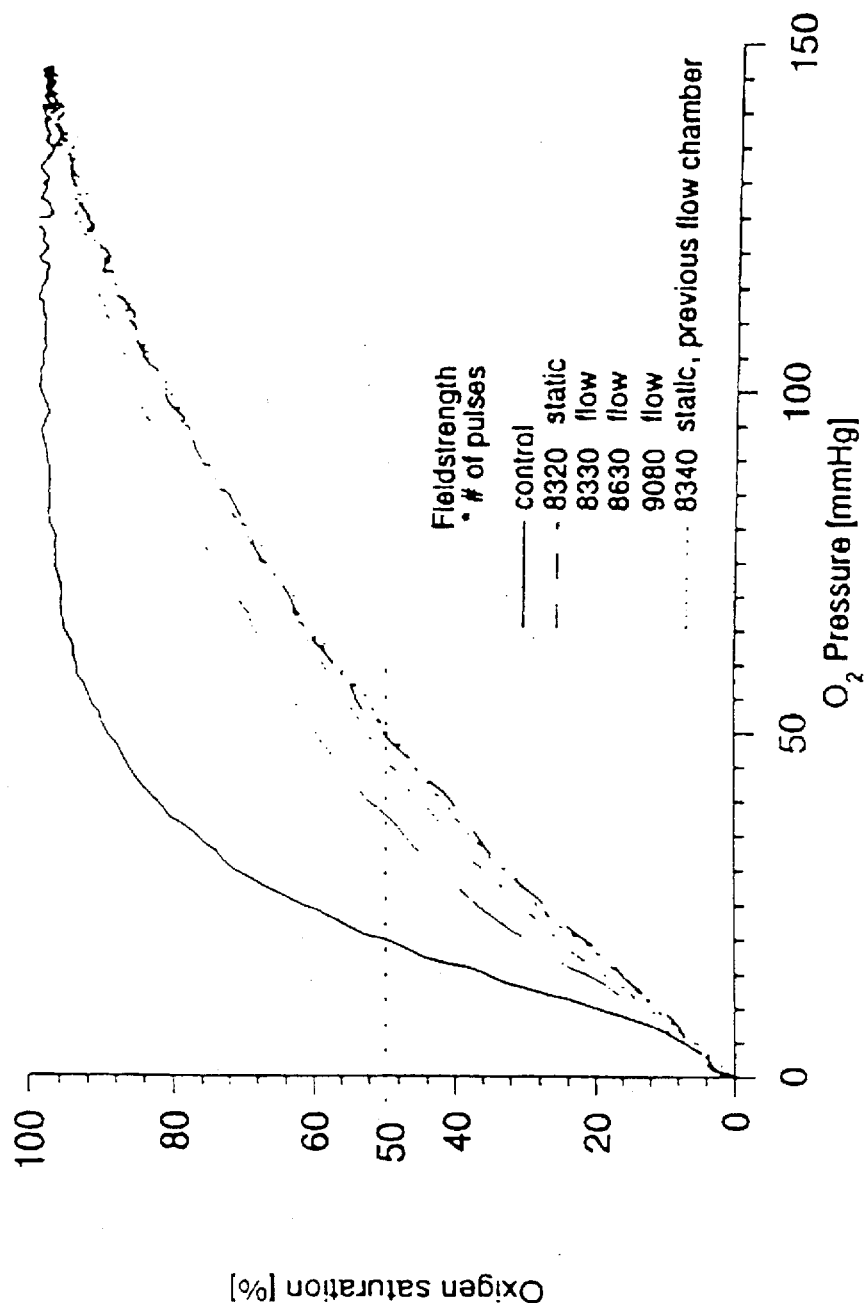
FIG. 11 is a graph comparing the effect of various field strengths, under static or flow conditions, on the % oxygenation of IHP-encapsulated red blood cells.
Figure 12:
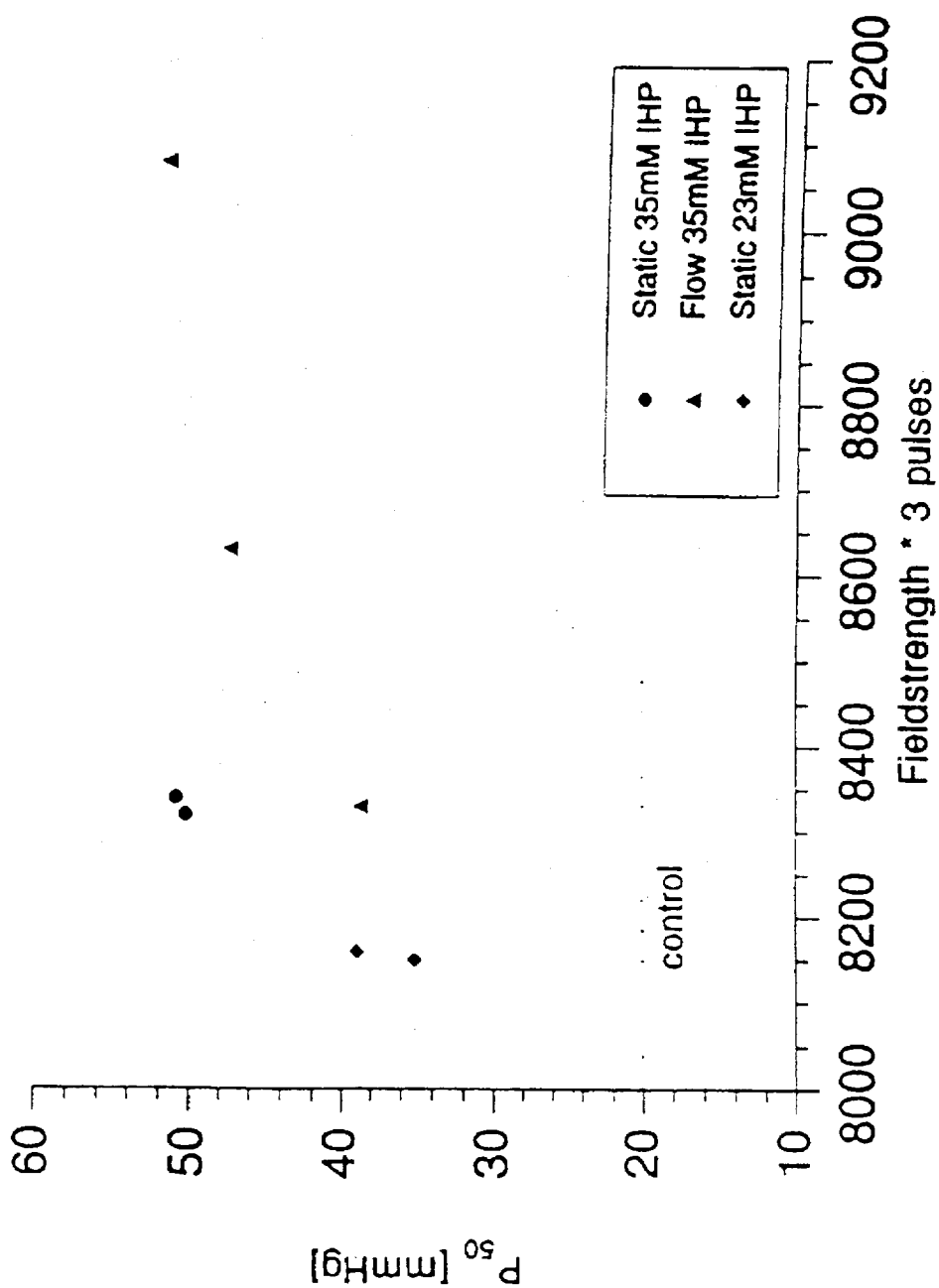
FIG. 12 is a table comparing the effects of various field strengths, under static or flow conditions, on the $P_{50}$ value of IHP-encapsulated red blood cells.
Figure 13:
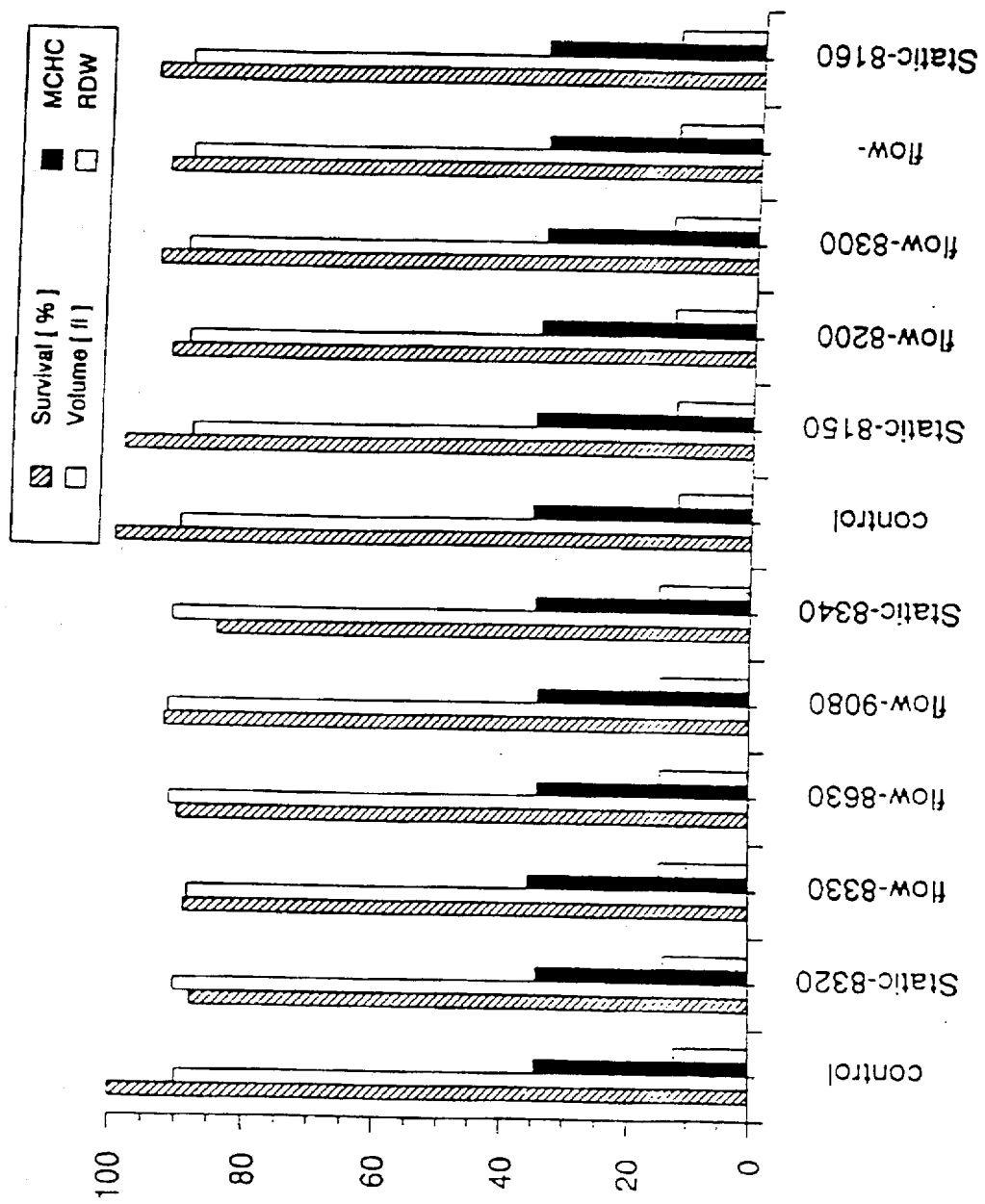
FIG. 13 is a table comparing the survival rates of red blood cells subjected to electroporation under static and flow conditions at various field strengths.

FIGS. 11 to 13 illustrate the effects of various field strengths, under static or flow conditions, on the % oxygenation of IHP-encapsulated red blood cells over a range oxygen pressures; on the $P_{50}$ value of IHP-encapsulated red blood cells (two concentrations of IHP solutions were compared); and, on the survival rates of red blood cells subjected to electroporation. All readings were taken 24 hours after electroporation. The results indicated that multiple pulses at comparatively low fieldstrengths produce optimal encapsulation results.

A cooled electroporation chamber is preferred to keep the red blood cells at a constant temperature during the electroporation process, thereby enhancing their survival rates. This is accomplished by removing the excess heat created by the electrical pulse during the electroporation process. The excess heat may be removed either by cooling the electrodes or cooling the entire flow electroporation chamber. In accordance with one embodiment of the present invention, the electrodes themselves are cooled.

During the electroporation process, blood is pumped through an inlet in the electroporation chamber and the red blood cells are subject to a series of electrical pulses as they travel through the chamber. They exit out the other end of the chamber. The chamber can be made of any type of insulating material, including, but not limited to, ceramic, Teflon, Plexiglas, glass, plastic, silicon, rubber or other synthetic materials. Preferably, the chamber is comprised of glass or polysulfone. Whatever the composition of the chamber, the internal surface of the chamber should be smooth to reduce turbulents in the fluid passing through it. The housing of the chamber should be non-conductive and biologically inert. In commercial use, it is anticipated that the chamber will be disposable.

In one preferred embodiment of the present invention, the electrodes that comprise part of the electroporation apparatus can be constructed from any type of electrically or thermally conductive hollow stock material, including, but not limited to, brass, stainless steel, gold plated stainless steel, gold plated glass, gold plated plastic, or metal containing plastic. Preferably, the surface of the electrode is gold plated. Gold plating serves to eliminate oxidation and reduces the collection of hemoglobin and other cell particles at the electrodes. The surface of the electrodes should be smooth.

The electrodes can be hollow, to allow cooling by liquid or gas, or the electrodes can be solid, to allow for thermoelectric or any other type of conductive cooling. Cooling could also be accomplished by cooling the electroporation chamber itself, apart from cooling the electrodes.

Preferably, the flow electroporation chamber is disposable. A detailed description of three embodiments of the electroporation chamber of the present invention is provided below.

In one embodiment, the flow electroporation chamber is constructed of clear polyvinyl chloride, and contains two opposing electrodes spaced a distance of approximately 7 mm apart. The electroporation chamber is a modification of a chamber obtained from BTX Electronic Company of San Diego, Calif. However, when this electroporation chamber is used continuously, it overheats and the survival rate of the cells processed by the apparatus decreases over time. To correct the overheating problem that occurred when the apparatus was used in a continuous flow manner, a continuous flow electroporation chamber was designed. A detailed description of the structure of the continuous flow electroporation chamber is provided below.

FIGS. 3 through 8 show one embodiment of the flow electroporation chamber 72 of the present invention. As can be seen in FIG. 3, the flow electroporation chamber 72 includes a housing 100 having two electrodes 102 inset on opposing sides of the housing 100 of the electroporation chamber 72. The housing 100 includes an inlet channel 104 at one end and an outlet channel 106 at the other. The inlet 104 and outlet 106 channels include connectors 108 and 109 respectively, preferably of the male Luer variety. The connectors 108 and 109 are hollow and form the inlet 104 and outlet 106 channels into the interior of the electroporation chamber 72.

As seen in FIGS. 4 and 5, an internal chamber 110 extends most of the length of the housing 100 and is sized to receive the two electrodes 102. The internal chamber 110 includes beveled surfaces 111 for receiving the internal edges of the electrodes 102. The internal chamber 110 is thus formed by the internal surfaces of the electrodes 102 and the internal surfaces of the housing 100. The internal chamber 110 is connected to the inlet 104 and outlet 106 channels.

Figure 8:
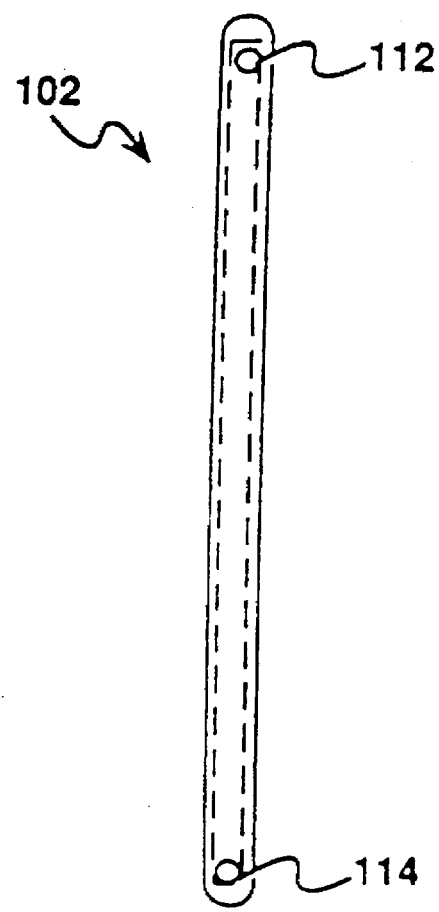
FIG. 8 is a front view of the electrode of FIG. 7.

As can be seen in FIGS. 7 and 8, the electrodes 102 of the electroporation chamber 72 of FIGS. 3 to 6 are comprised of flat, elongated, hollow shells. The electrodes 102 include cooling inlets 112 and cooling outlets 114 at their ends. As described above, the rear surfaces of the electrodes 102, or the surface to the left in FIG. 7, fits flush against the beveled surface 111 of the housing 100.

The electroporation chamber 72 is designed such that the cell suspension to be subjected to electroporation enters the electroporation chamber 72 through the inlet 104 and expands to fill the internal chamber 110. As the red blood cell suspension flows through the internal chamber 110 a pulse or charge is administered across the width of the internal chamber 110.

To maintain a relatively constant temperature during the electroporation process, cooling fluid or cooling gas is pumped in the cooling inlet 112 and out the cooling outlet 114 so that the electrodes 102 are maintained at approximately 4° C.

FIGS. 9 and 10 display a second embodiment of the flow electroporation chamber 172. As can be seen in FIGS. 9 and 10, the flow electroporation chamber 172 includes a hollow housing 200 substantially rectangular in shape. Two electrodes 202 are inserted into the interior of the housing 200 directly opposite one another, flush against the housing 200 walls. The flow electroporation chamber 172 further comprises an inlet channel 204 at one end and an outlet channel 206 at the other end of the housing 200. The inlet 204 and outlet 206 channels include connectors 208 and 209 which are attached by tubing 216 to a cell suspension supply that supplies the cell suspension, i.e. the IHP-red blood cell suspension, to the electroporation chamber 172. The connectors 208 and 209 and inlet 204 and outlet 206 channels serve to direct the cell suspension into and out of the housing 200.

As can be seen in FIG. 10, one end of the inlet channel 204 and one end of the outlet channel 206 extends into the interior of the housing 200 forming an internal chamber 210. The internal chamber 210 is thus formed by the internal surfaces of the electrodes 202, the internal surfaces of the housing 200 and the internal surfaces of the of the inlet 204 and outlet 206 channels.

As can be seen in FIGS. 9 and 10, the electrodes 202 of the flow electroporation chamber 172 comprise flat, elongated, hollow shells. The electrodes 202 include cooling inlets 212 and cooling outlets 214 at their ends, through which a gas or fluid may be pumped through the electrodes 202 to maintain a constant temperature during electroporation. The electrodes 202 are connected to a pulse generator by cables 220.

As with the chamber described above, the electroporation chamber 172 of FIGS. 9 and 10 is designed such that the suspension to be subjected to electroporation enters the electroporation chamber 172 through the fluid inlet 204 and expands to fill the internal chamber 210. As the red blood cells suspension flows through the internal chamber 210, a pulse or charge is administered across the width of the internal chamber 210 between the electrodes 202. To maintain a relatively constant temperature during the electroporation process, cooling fluid or cooling gas is pumped in the cooling inlet 212 and out the cooling outlet 214 of the electrodes 202 through the connectors 208 and 209 so that the electrodes 202 are maintained at approximately 4° C. It is also possible that the inlet channel 204, outlet channel 206 and connectors 208 and 209 can be made as a solidly integrated glass part, rather than separate components.

It is contemplated that the flow electroporation chamber 172 maybe constructed from drawn glass or any other highly polished material. It is preferable that the interior surface of the electroporation chamber 172 be as smooth as possible to reduce the generation of surface turbulence. Drawn glass components are highly consistent with perfect surface finishes. Furthermore, they are stable and inert to blood components. They are also relatively inexpensive, which is desirable for a disposable electroporation chamber.

The electrodes may also be comprised of drawn glass, electroplated with colloidal gold. Again, the surfaces of the electrodes should be highly finished, highly conductive, yet biologically inert. Gold electroplate is durable and inexpensive. Fluidic connection can be accomplished using commonly available parts.

The flow electroporation chamber may be constructed either as a part of the entire flow encapsulation apparatus, or as an individual apparatus. The flow electroporation apparatus may then be connected to a commercially available plasmaphoresis machine for encapsulation of particular cell populations. For example, the flow electroporation chamber may be connected to commercially available plasmaphoresis equipment by electronic or translational hardware or software. Optionally, a pinch-valve array and controller driven by a PC program can also be used to control the flow electroporation apparatus. Similarly, current power supplies are capable of establishing the power levels needed to run the flow electroporation chamber or flow encapsulation apparatus.

A third embodiment of a continuous flow electroporation chamber will now be described with reference to FIGS. 14–20. Referring first to FIGS. 14–16, a support member 300 is comprised of flexible silicone rubber. The support structure 300 is essentially diamond shaped and comprises an upper end 301 and a lower end 302. A major portion of the support structure 300 has a grid-like "waffle" pattern formed on it, comprised of thicker rib sections 303 and thinner sections 304 intermediate the fibs 303. Along the marginal edges of the support structure 300, a plurality of tabs 305 are provided, each having a hole 306 formed therethrough.

A channel 308 extends between the upper end 301 and the lower end 302 of the support structure and lies along the major axis of the support structure 300. The channel 308 comprises opposed channel walls 310, 312 connected by a base 314. At the upper end 301 of the support structure 300 the channel 308 opens into a circular cavity 318. A hole 320 is formed in the center of the circular cavity 318. An outlet aperture 322 is provided at the upper end of the circular cavity 318. In a like manner, the lower end of the channel 308 opens into a circular cavity 324 formed in the lower end 302 of the support structure 300. A hole 326 is formed through the support structure in the center of the cavity 324, and an inlet aperture 328 is provided at the lower end of the circular cavity 324.

A pair of continuous band electrodes 330A, 330B comprised of conductive metallic tape or foil are located on the support structure 300. Each of the electrodes 330A, 330B has a portion which is disposed within the channel 308 and which runs substantially the entire length of the channel 308. As can perhaps best be seen in FIG. 16, electrodes 330A, 330B are received in opposing recesses 332 formed in the side walls 310, 312 of the channel 308. Adjacent the upper and lower ends of the channel 308, each of the continuous band electrodes 330A, 330B exits the channel 308 through a close fitting slit formed in the channel walls. The continuous band electrodes 330A, 330B then curve outward and extend substantially parallel to the periphery of the support member 300 and spaced inward therefrom. Along the midline of the support structure 300 and adjacent its outer edges, a slack portion 334 is provided in each of the continuous band electrodes 330A, 330B, for the purposes to be described below.

On either side of the channel 308 and immediately adjacent thereto, a plurality of generally rectangular holes 340 are formed. As will be more fully explained below, the holes 340 are located to accommodate Peltier thermo-electric elements for cooling purposes. On either side of the channel 308 adjacent its upper and lower ends, circular holes 342 are provided which, as will be shown, are adapted to receive capstans for tensioning the continuous band electrodes 330A, 330B. Along the midline of the support structure 300 and adjacent its outer edges, a pair of holes 344 which, as will be more fully explained below, are adapted to receive electrical contacts therethrough for charging the electrodes 330A, 330B.

Referring now to FIG. 17, the support member 300 is mounted to a transparent polycarbonate frame 350. The frame 350 comprises a planar front wall 352. Interior side walls 354 extend rearward from the lateral edges of the planar front wall 352. A rearward opening channel 356 is formed between the two interior side walls 354. At the rear edges of the interior side walls 354, a pair of back walls 358 extend outward. A pair of exterior side walls 360 extend forward from the outer edges of the back walls 358. Forward opening channels 362 are formed between the exterior side walls 360 and the interior side walls 354. Rods 363 removably mounted in each of the forward opening channels 362 provide a convenient means for hanging fluid storage bags within the channels.

The support structure 300 is mounted to the back surface of the front wall 352 of the polycarbonate frame 350. The support structure 300 is adhesively bonded to the frame 350 such that the front wall 352 of the frame 350 seals the open upper end of the channel 308 formed in the face of the support structure 300. Thus enclosed, the channel 308 defines a fluid passage or "flow cell" 364. In addition, the support structure 300 and associated portion of the frame 350 define an electroporation chamber 366.

Referring further to FIG. 17, a support column 370 has a generally rectangular cross section. In the front face 371 of the support column 370 a cavity 372 is formed which conforms to the shape and depth of the support structure 300. Spaced on either side and along the major axis of the cavity 372, a plurality of bismuth telluride Peltier thermoelectric elements 374 are fixedly mounted in the cavity and project forward from the base of the cavity 372. The Peltier thermo-electric elements 374 are in thermal communication with a heat sink 375 mounted inside the support column 370. An electric fan 376 mounted in an adjacent portion of the support column 370 creates a flow of air through the column to dissipate heat away from the heat sink 375.

Adjacent the upper and lower ends of the cavity 372 and spaced to either side of the center line are capstans 377. Adjacent the outer edges of the cavity 372 and located along the minor axis of the cavity are a pair of electrode contacts 378. Located just inside the perimeter of the cavity 372 are eight locator pins 379, two of the locator pins 379 being situated along each of the four walls of the diamond-shaped cavity. At the upper and lower ends of the cavity 372 and located on the major axis of the cavity are a pair of hollow, porous, polymeric cylinders 380. The cylinders 380 are preferably formed of inert foamed polyethylene (such as Porex) with a pore size permitting passage of gas but not liquid. As will be more fully explained hereinbelow, these gas-permeable, liquid impermeable cylinders function as a means for removing bubbles from fluid passing thereover.

The dimensions of the polycarbonate frame 350 are such that the support column 370 is snugly received within the rearward opening channel 356 of the frame. As the frame 350 is positioned onto the support column 370, the support structure 300 mounted to the back surface of the front wall 352 of the frame 350 fits within the cavity 372 formed in the front face 371 of the support column 370. A shelf 381 is located on the front face 371 of the support column 370 immediately below the cavity 372 to support the lower edge of the polycarbonate frame 350.

Figure 19:
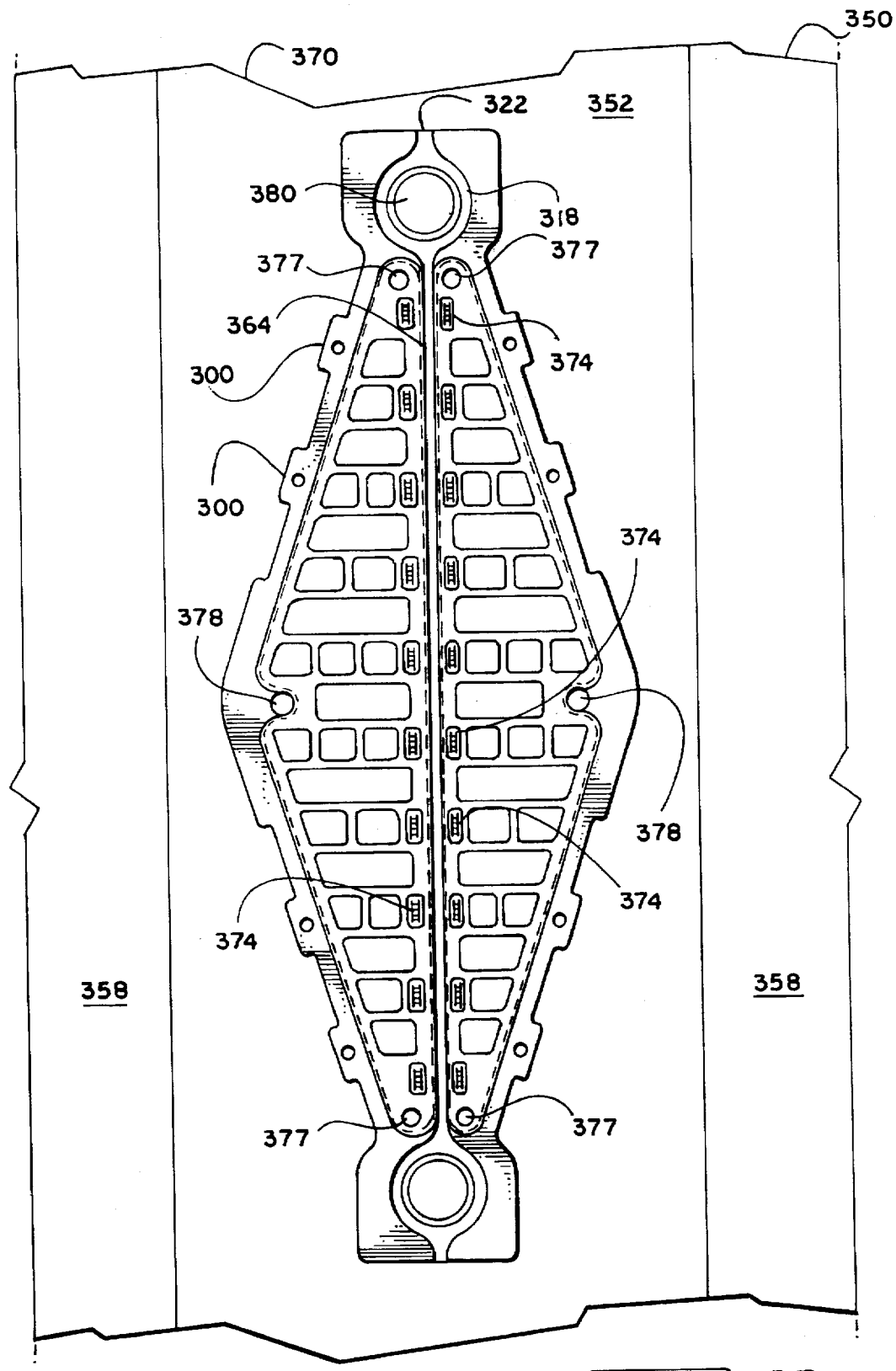
FIG. 19 is a front elevation view of the electroporation chamber according to the third embodiment mounted to a support column.

With the frame 350 thus mounted to the support column 370, the various elements associated with the cavity 372 and the support column 370 cooperatively engage the support structure 300 as shown in FIG. 19. Specifically, the thermoelectric cooling elements 374 project through the holes 340 in the support structure 300 and contact the walls of the channel 308. The capstans 377 extend through the holes 342 in the upper and lower ends of the support structure 300. The electrode contacts 378 project through the holes 344 in the support structure 300. The locator pins 379 are received within the corresponding holes 306 in the tabs 305 of the support member 300. And the gas-permeable, liquid impermeable cylinders 380 extend through the holes 320, 326 in the cavities 318, 324 at the upper and lower ends 301, 302 of the support structure 300.

Referring now to FIG. 20, at least one of the capstans 377 supporting each of the electrodes 330A, 330B is tensioned such as by tensioning means 382 to maintain the continuous band electrodes in a taut state. As can also be seen in FIG. 20, each electrode contact 378 has a slot 383 formed in its face, and the slack section 334 of the associated continuous band electrode 330A or 330B is threaded through this slot. A motor 384 in driving engagement with each electrode contact 378 can be operated to rotate the electrode contact, thereby winding the electrode 330A or 330B around a portion of the contact and taking up the slack. This winding action serves the additional function of increasing surface contact between the electrode contact 378 and its associated electrode 330A or 330B, thereby enhancing the electrical connection to the electrodes.

The gas permeable, liquid impermeable cylinders 380 at the upper and lower ends of the flow cell 364 (only the upper of which is shown in FIG. 20) are in fluid communication with a vacuum source by way of a coupling 388 and tubing 390. Also shown in FIG. 20, the heat sinks 375 dissipate the heat collected by the thermo-electric cooling elements 374.

Control of fluid flow along the appropriate flow paths into and out of the flow cell 364 is accomplished by peristaltic pumping means 392 and solenoid-activated pinch valves 394, mounted in the support column 350. The pumping means 392 and pinch valves 394 operate under control of appropriate algorithms in computer means (not shown) operably connected thereto.

A cooled plate 396 is mounted on the side of the support column 370. A cooling bag 398 retained in the channel 362 of the frame 350 is held in intimate contact with this plate 396 to cool treated fluids following electroporation. Depending upon the circumstances and the biological substance being treated, the plate 396 may optionally be heated to maintain the contents of the bag 398 at a predetermined temperature above that of the ambient.

FIG. 21 illustrates a self-contained electroporation apparatus 400. The apparatus 400 comprises a cart 402 which serves as a housing and support structure. The support column 370 with electroporation chamber 366 is mounted to the cart and extends upward therefrom. The cart 402 has a chassis structure 404, which is provided with wheels 406 to facilitate transport of the cart 402 from one location to another. Mounted to the chassis structure 404 are power supply capacitors 408. A power supply heatsink 410 is in thermal communication with the power supply capacitors 408 to dissipate the heat generated by the power supply capacitors.

A circuitboard computation means 412 is also mounted within the chassis structure 404. The circuitboard computation means 412 is powered by a power supply circuit board 414 mounted within the chassis structure 404 adjacent the circuitboard computation means. A power supply heatsink 416 in thermal communication with the power supply circuit board 414 dissipates the heat generated by the power supply circuit board. A cooling fan 418 mounted at the lower end of the front panel 420 of the chassis structure 404 pulls air through the chassis structure to draw heat away from the heatsinks 410, 416.

A system status display 422 operatively associated with the circuitboard computation means 412 is mounted to the front panel 420 of the cart 402. Control switches 424 for setting various parameters of the circuitboard computation means 412 are mounted to the front panel 420 of the cart 402 below the system status display 422.

Mounted within the top panel 428 of the cart 402 is a centrifuge bowl 430. A centrifuge drive motor 432 mounted within the chassis structure 404 is in driving engagement with the centrifuge bowl 430. The centrifuge bowl 430 includes a rotary connector 434 through which blood is input into the centrifuge bowl.

Treatment of biological particles in the self-contained electroporation apparatus 400 comprising the electroporation chamber 366 of the third embodiment will now be described with reference to FIG. 21. A blood supply bag 450 is hung on a rod 363 within one of the channels 362 of the frame 350. A tubing 452 transports the blood to the centrifuge bowl 430, where it is introduced into the centrifuge bowl through a rotary connector 434. The blood is centrifuged to separate the red blood cells from the plasma, white blood cells, and waste. The red blood cells are then admixed with the substance to be encapsulated. The admixture is transported via a tubing 454 and introduced into the inlet aperture 328 at the lower end of the cell 364. The admixture is caused to flow upward through the flow cell 364 between the electrodes 330A, 330B. The electrodes are charged in a pulsed manner, as hereinabove described with respect to the second embodiment. Gases in the admixture resulting from electrolysis are removed by the gas-permeable, liquid impermeable cylinders 380 at the upper and lower ends of the cell. The treated admixture exits the outlet aperture 324 at the upper end of the cell, and an outlet tubing 456 transports the treated admixture to a cooling bag 460 suspended on a rod 363 within another one of the channels 362 of the frame 350 and in contact with the cooled plate 396. The fluid is then conveyed to a post-treatment cooling and storage bag 462 suspended on the rod 363 next to the cooling bag 460.

Pump speeds (and hence flow rates), valve operation, centrifuge operation, operation of the Peltier thermo-electric elements, and pulsed charging of the electrodes are all controlled by the circuitboard computation means 412. Ideally, the processing rate of the centrifuge bowl 430 is matched to the flow rate of the flow cell 364. However, to accommodate any mismatch, a reservoir may optionally be provided between the centrifuge bowl 430 and the flow cell 364. Thus if the centrifuge bowl 430 processes the blood faster than the flow cell 364 can process it, the reservoir will hold any excess admixture until the flow cell can "catch up." Similarly, if the centrifuge bowl 430 processes the blood slower than the flow cell 364 can process it, the circuitboard computation means 412 can initially accumulate admixture in the reservoir. Then when the centrifuge bowl 430 has processed a sufficient volume of blood, admixture can be transported from the reservoir to the flow cell 364. By the time the volume of admixture in the reservoir has been depleted, the centrifuge bowl will have completed processing the desired quantity of blood.

An optional feature of the electroporation apparatus 400 hereinabove described is that the series of Peltier thermoelectric cooling elements 374 can be individually controllable, such that cooling elements 374 at one location along the flow cell 364 can provide a greater or lesser degree of cooling than other cooling elements 374 at other locations along the flow cell 364. Since the biological particles are being heated as they move along the flow cell 364, more cooling may be necessary closer to the discharge end of the flow cell 364 than is necessary adjacent the input end. Providing individual control over the various thermoelectric cooling elements 374 permits accommodation of these variations. The various thermo-electric cooling elements 374 can be controlled either by placing thermal sensors at various locations along the flow cell, inputting the sensed temperatures into the circuitboard computation means 412, and controlling the various thermo-electric cooling elements in response to the sensed temperatures. Or, the various thermo-electric cooling elements 374 can be controlled according to a predetermined "average" temperature variance of the biological particles along the flow cell. Other methods for controlling various thermo-electric cooling elements 374 will occur to those skilled in the art.

As will be appreciated by those familiar with the art, there are several reasons why it is not desirable to re-use an electroporation cell. First, the possibility exists that infectious components could be transferred to other patients. Further, electrical performance of the electrode surfaces would degrade due to the high voltage potentials across these surfaces, thereby increasing the potential for arcing. To prevent these and other problems, a feature of this third disclosed embodiment provides a means for ensuring that the cell is not re-used. At the termination of the procedure, and before the frame 350 is removed from the support column 370, the motors 384 in driving engagement with the electrode contacts 378 are automatically actuated to over-rotate, tensioning the electrodes 330A, 330B beyond their tensile strength and breaking them. With the electrodes 330A, 330B thus broken, re-use of the cell is impossible.

A known risk associated with electroporation apparatus is the unintentional production of gases by electrolysis. Overpressures resulting from the unwanted buildup of such gases have been known to result in explosive expression. To minimize this possibility, the present invention employs a flow cell 364 defined on three sides by soft silicone rubber. In the event of transient overpressures, the elasticity of the support structure 300 will accommodate expansion of the flow cell 364 and thereby reduce the possibility of explosion. In addition, the flow cell 364 is sandwiched tightly between the support column 370 and the polycarbonate frame 350, providing further protection against any possible explosive expression.

While this invention has been described in specific detail with reference to the disclosed embodiments, it will be understood that many variations and modifications may be effected within the spirit and scope of the invention as described in the appended claims.

Application of IHP treated red blood cells

The present invention provides a novel method for increasing the oxygen-carrying capacity of erythrocytes. In accordance with the method of the present invention, the IHP combines with hemoglobin in a stable way, and shifts its oxygen releasing capacity. Erythrocytes with IHP-hemoglobin can release more oxygen per molecule than hemoglobin alone, and thus more oxygen is available to diffuse into tissues for each unit of blood that circulates. Under ordinary circumstances, IHP is toxic and cannot be tolerated as an ordinary drug. Attachment of IHP to hemoglobin in this novel procedure, however, neutralizes its toxicity. In the absence of severe chronic blood loss, treatment with a composition prepared in accordance with the present method could result in beneficial effects that persist for approximately ninety days.

Another advantage of IHP-treated red blood cells is that they do not lose the Bohr effect when stored. Normal red blood cells that have been stored by conventional means do not regain their maximum oxygen carrying capacity for approximately 24 hours. This is because the DGP in normal red blood cells diffuses away from the hemoglobin molecule during storage and must be replaced by the body after transfusion. In contrast, red blood cells treated according to the present invention are retain their maximum oxygen carrying capacity during storage and therefore can deliver maximum oxygen to the tissues immediately after transfusion into a human or animal.

The uses of IHP-treated RBC's is quite extensive including the treatment of numerous acute and chronic conditions including, but not limited to, hospitalized patients, cardiovascular operations, chronic anemia, anemia following major surgery, coronary infarction and associated problems, chronic pulmonary disease, cardiovascular patients, autologous transfusions, as an enhancement to packed red blood cells transfusion (hemorrhage, traumatic injury, or surgery). congestive heart failure, myocardial infarction (heart attack), stroke, peripheral vascular disease, intermittent claudication, circulatory shock, hemorrhagic shock, anemia and chronic hypoxmia, respiratory alkalemia, metabolic alkalosis, sickle cell anemia, reduced lung capacity caused by pneumonia, surgery, pneumonia, trauma, chest puncture, gangrene, anaerobic infections, blood vessel diseases such as diabetes, substitute or complement to treatment with hyperbaric pressure chambers, intra-operative red cell salvage, cardiac inadequacy, anoxia—secondary to chronic indication, organ transplant, carbon monoxide, nitric oxide, and cyanide poisoning.

Treating a human or animal for any one or more of the above disease states is done by transfusing into the human or animal between approximately 0.5 and 6 units (1 unit= 500 ml) of IHP-treated blood that has been prepared according to the present invention. In certain cases, there may be a substantially complete replacement of all the normal blood in a patient with IHP-treated blood. The volume of IHP-treated red blood cells that is administered to the human or animal will depend upon the indication being treated. In addition, the volume of IHP-treated red blood cells will also depend upon concentration of IHP-treated red blood cells in the red blood cell suspension. It is to be understood that the quantity of IHP red blood cells that is administered to the patient is not critical and can vary widely and still be effective.

IHP-treated packed RBC's are similar to normal red blood cells in every category except that the IHP-treated packed red blood cells can deliver 2 to 3 times as much oxygen to tissue per unit. A physician would therefore chose to administer a single unit of IHP-treated packed red blood cells rather than 2 units of the normal red blood cells. IHP-treated packed red blood cells could be prepared in blood processing centers analogously to the present blood processing methods, except for the inclusion of a processing step where the IHP is encapsulated in the cells.

While this invention has been described in specific detail with reference to the disclosed embodiments, it will be understood that many variations and modifications may be effected within the spirit and scope of the invention as described in the appended claims.

What is claimed is:

1. Apparatus for poration of biological particles, comprising:

walls defining a fluid flow path;

electrodes disposed along opposing sides of said fluid flow path, said electrodes including means for placing said electrodes in electrical communication with a source of pulsed electrical energy, whereby biological particles moving along said fluid flow path are subjected to a pulsed electrical field;

said apparatus being characterized by at least one of said walls defining said fluid flow path being elastically deformable and at least another one of said walls defining said fluid flow path being substantially rigid; whereby transient pressure increases within said fluid flow path are at least partially absorbed by said elastic material of said wall.

2. The electroporation chamber of claim 1, wherein said at least one of said walls defining said fluid flow path being comprised of a deformable, elastic material comprises two of said walls being comprised of a deformable, elastic material.

3. The electroporation chamber of claim 1, wherein said electrodes comprise continuous band electrodes.

4. Apparatus for poration of biological particles, said apparatus being removably mounted to a support member, said apparatus comprising:

walls defining a fluid flow path;

electrodes disposed along opposing sides of said fluid flow path, said electrodes including means for placing said electrodes in electrical communication with a source of pulsed electrical energy, whereby biological particles moving along said fluid flow path are subjected to a pulsed electrical field; and means connected to said electrodes when said apparatus is mounted to a support member for destroying said electrodes prior to said apparatus being removed from said support member;

whereby said apparatus cannot be re-used.

5. The electroporation chamber of claim 4, wherein said means for placing said electrodes in electrical communication with a source of energy comprises a spindle, said electrodes being wrapped around at least a portion of the periphery of an associated spindle; and wherein said means for destroying said electrodes comprises means for rotating said spindles so as to stretch said electrodes beyond their tensile limits, thereby rupturing said electrodes and rendering them electrically inoperative.

6. Apparatus for poration of biological particles, comprising:

walls defining a fluid flow path;

electrodes disposed along opposing sides of said fluid flow path, said electrodes including means for placing said electrodes in electrical communication with a source of pulsed electrical energy, whereby biological particles moving along said fluid flow path are subjected to a pulsed electrical field;

pump means for moving said biological particles along said fluid flow path; and control means responsive to the rate at which said pump moves said biological particles along said fluid flow path for controlling the interval between pulses of said electrical energy, whereby said biological particles moving along said fluid flow path are exposed to a predetermined number of pulses during their exposure between said electrodes.

* * * * *